United States Patent
Cosson et al.

(10) Patent No.: US 9,745,357 B2
(45) Date of Patent: Aug. 29, 2017

(54) PEPTIDES USED FOR TREATING CANCERS AND, IN PARTICULAR, CHRONIC LYMPHOID LEUKAEMIA

(75) Inventors: Bertrand Cosson, Taulë (FR); Hussam Saad, Treflaouenan (FR); Patrick Cormier, Cléder (FR); Christian Berthou, Brest (FR); Mirjam Czjzek, Plougoulm (FR)

(73) Assignees: Centre National de la Recherche Scientifique, Paris (FR); Centre Hospitalier Universitaire de Brest, Brest (FR); Universite de Bretagne Occidentale, Brest (FR); Universite Pierre et Marie Curie (Paris 6), Paris (FR)

( * ) Notice: Subject to any disclaimer, the term of this patent is extended or adjusted under 35 U.S.C. 154(b) by 1443 days.

(21) Appl. No.: 13/203,777

(22) PCT Filed: Mar. 5, 2010

(86) PCT No.: PCT/FR2010/000191
§ 371 (c)(1),
(2), (4) Date: Nov. 14, 2011

(87) PCT Pub. No.: WO2010/100351
PCT Pub. Date: Sep. 10, 2010

(65) Prior Publication Data
US 2012/0172315 A1   Jul. 5, 2012

(30) Foreign Application Priority Data
Mar. 5, 2009  (FR) ..................... 09 01007

(51) Int. Cl.
| A61K 38/10 | (2006.01) |
| A61K 38/12 | (2006.01) |
| A61P 35/00 | (2006.01) |
| A61P 35/02 | (2006.01) |
| C07K 7/08  | (2006.01) |
| C07K 7/64  | (2006.01) |
| C07K 14/47 | (2006.01) |

(52) U.S. Cl.
CPC .................... *C07K 14/47* (2013.01)

(58) Field of Classification Search
None
See application file for complete search history.

(56) References Cited

U.S. PATENT DOCUMENTS

2006/0223088 A1* 10/2006 Rosen et al. ............... 435/6

FOREIGN PATENT DOCUMENTS

| WO | WO00/18895    | * | 4/2000  |
| WO | WO00/78803    | * | 12/2000 |
| WO | WO03/059942   | * | 7/2003  |
| WO | WO2005/081911 | * | 9/2005  |
| WO | WO2007/098415 | * | 8/2007  |
| WO | 2007/150077   |   | 12/2007 |
| WO | 2008/150689   |   | 12/2008 |

OTHER PUBLICATIONS

Lu et al (The AAPS Journal, 2006, vol. 3, Issue 3, Article 55 pp. E466-E478).*
Foged and Nielsen (Expert Opinion on Drug Delivery, 2008, vol. 5, pp. 105-111).*
Gosselin et al, Nucleic Acids Research, 2013, vol. 14, pp. 7783-7792.*
Gingras, eIF4 Initiation Factors: Effectors of mRNA Recruitment to Ribosomes and Regulators of Translation, Annual Review of Biochemistry, 68, 913-963, 1999.
Saad, eIF4 Initiation Factors: From Sea Urchin Embryonic Development to Chronic Lymphocytic Leukemia, Journal de la Societe de Biologie, 201, 307-315, 2007 (See English language abstract).
Schmitt, PHAMM-R3 Peptide Vaccination in Patients with Acute Myeloid Leukemia, Myelodysplastic Syndrome, and Multiple Myeloma Elicits Immunologic and Clinical Responses, Blood, 111, 1357-1365, 2007.
Greiner, High-Dose RHAMM-R3 Peptide Peptide Vaccination for Patients with Vaccination for Patients with Acute Myeloid Leukemia (AML), Myelodysplastic Syndrome (MDS), Multiple Myeloma (MM) and Chronic Lymphoicytic Leukemia (CLL), Blood, 112, 2911, 2008.

* cited by examiner

*Primary Examiner* — Karen Canella
(74) *Attorney, Agent, or Firm* — Morgan, Lewis & Bockius LLP

(57) ABSTRACT

The invention relates to the A1 peptide of the sequence RRKYGRDFLLRF, as well as to certain variants thereof, for treating cancers, in particular malignant hematopoietic diseases, and more particularly for treating chronic lymphoid leukaemia.

19 Claims, 9 Drawing Sheets

Figure 1:
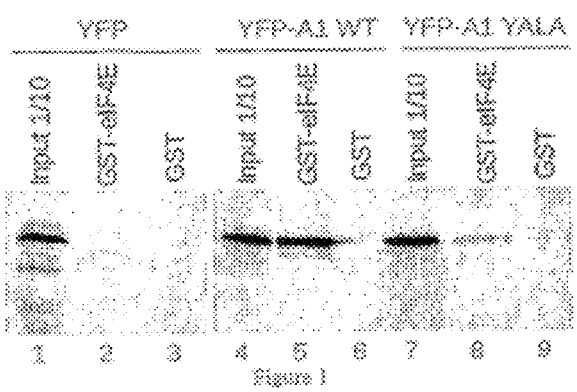

SEQUENCE LISTING

```
<160> NUMBER OF SEQ ID NOS: 30

<210> SEQ ID NO 1
<211> LENGTH: 12
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: can be replaced with = "Lys" or "His"
<220> FEATURE:
<221> NAME/KEY: VARIANT
<222> LOCATION: (2)..(2)
<223> OTHER INFORMATION: can be replaced with = "Lys" or "His"
<220> FEATURE:
<221> NAME/KEY: VARIANT
<222> LOCATION: (3)..(3)
<223> OTHER INFORMATION: can be replaced with = "Arg" or "His"
<220> FEATURE:
<221> NAME/KEY: VARIANT
<222> LOCATION: (5)..(5)
<223> OTHER INFORMATION: can be replaced with any amino acid
<220> FEATURE:
<221> NAME/KEY: VARIANT
<222> LOCATION: (6)..(6)
<223> OTHER INFORMATION: can be replaced with any amino acid
<220> FEATURE:
<221> NAME/KEY: VARIANT
<222> LOCATION: (7)..(7)
<223> OTHER INFORMATION: can be replaced with any amino acid
<220> FEATURE:
<221> NAME/KEY: VARIANT
```

-continued

```
<222> LOCATION: (8)..(8)
<223> OTHER INFORMATION: can be replaced with = "Ala" or "Val" or
      "Leu" or "Ile" or "Met"
<220> FEATURE:
<221> NAME/KEY: VARIANT
<222> LOCATION: (10)..(10)
<223> OTHER INFORMATION: can be replaced with = ""Met" or "Phe"
<220> FEATURE:
<221> NAME/KEY: VARIANT
<222> LOCATION: (11)..(11)
<223> OTHER INFORMATION: can be replaced with any amino acid
<220> FEATURE:
<221> NAME/KEY: VARIANT
<222> LOCATION: (12)..(12)
<223> OTHER INFORMATION: can be replaced with = "Tyr" or "Trp" or "His"

<400> SEQUENCE: 1

Arg Arg Lys Tyr Gly Arg Asp Phe Leu Leu Arg Phe
1               5                   10

<210> SEQ ID NO 2
<211> LENGTH: 17
<212> TYPE: PRT
<213> ORGANISM: Artificial
<220> FEATURE:
<223> OTHER INFORMATION: Synthetic peptide

<400> SEQUENCE: 2

Arg Arg Lys Tyr Gly Arg Asp Phe Leu Leu Arg Phe Arg Tyr Ile Arg
1               5                   10                  15

Ser

<210> SEQ ID NO 3
<211> LENGTH: 12
<212> TYPE: PRT
<213> ORGANISM: Artificial
<220> FEATURE:
<223> OTHER INFORMATION: Synthetic peptide

<400> SEQUENCE: 3

Arg Arg Lys Tyr Gly Arg Asp Phe Leu Leu Arg Phe
1               5                   10

<210> SEQ ID NO 4
<211> LENGTH: 5
<212> TYPE: PRT
<213> ORGANISM: Artificial
<220> FEATURE:
<223> OTHER INFORMATION: Synthetic peptide

<400> SEQUENCE: 4

Arg Tyr Ile Arg Ser
1               5

<210> SEQ ID NO 5
<211> LENGTH: 12
<212> TYPE: PRT
<213> ORGANISM: Artificial
<220> FEATURE:
<223> OTHER INFORMATION: Synthetic peptide

<400> SEQUENCE: 5

Arg Arg Lys Ala Gly Arg Asp Phe Ala Ala Arg Phe
1               5                   10

<210> SEQ ID NO 6
<211> LENGTH: 17
<212> TYPE: PRT
```

```
<213> ORGANISM: Artificial
<220> FEATURE:
<223> OTHER INFORMATION: Synthetic peptide

<400> SEQUENCE: 6

Arg Arg Lys Ala Gly Arg Asp Phe Ala Ala Arg Phe Arg Tyr Ile Arg
1               5                   10                  15

Ser

<210> SEQ ID NO 7
<211> LENGTH: 17
<212> TYPE: PRT
<213> ORGANISM: Artificial
<220> FEATURE:
<223> OTHER INFORMATION: Synthetic peptide

<400> SEQUENCE: 7

Arg Ile Ile Tyr Asp Arg Lys Phe Leu Leu Asp Arg Tyr Ile Arg
1               5                   10                  15

Ser

<210> SEQ ID NO 8
<211> LENGTH: 17
<212> TYPE: PRT
<213> ORGANISM: Artificial
<220> FEATURE:
<223> OTHER INFORMATION: Synthetic peptide

<400> SEQUENCE: 8

Arg Ile Ile Ala Asp Arg Lys Phe Ala Ala Asp Arg Arg Tyr Ile Arg
1               5                   10                  15

Ser

<210> SEQ ID NO 9
<211> LENGTH: 17
<212> TYPE: PRT
<213> ORGANISM: Artificial
<220> FEATURE:
<223> OTHER INFORMATION: Synthetic peptide

<400> SEQUENCE: 9

Arg Ile Ile Tyr Asp Arg His Phe Leu Leu Asn Met Arg Tyr Ile Arg
1               5                   10                  15

Ser

<210> SEQ ID NO 10
<211> LENGTH: 17
<212> TYPE: PRT
<213> ORGANISM: Artificial
<220> FEATURE:
<223> OTHER INFORMATION: Synthetic peptide

<400> SEQUENCE: 10

Arg Ile Ile Ala Asp Arg His Phe Ala Ala Asn Met Arg Tyr Ile Arg
1               5                   10                  15

Ser

<210> SEQ ID NO 11
<211> LENGTH: 17
<212> TYPE: PRT
<213> ORGANISM: Artificial
<220> FEATURE:
<223> OTHER INFORMATION: Synthetic peptide
```

<400> SEQUENCE: 11

Arg Arg Ile Tyr Gly Arg Asp Phe Leu Leu Arg Phe Arg Tyr Ile Arg
1               5                   10                  15
Ser

<210> SEQ ID NO 12
<211> LENGTH: 15
<212> TYPE: PRT
<213> ORGANISM: Artificial
<220> FEATURE:
<223> OTHER INFORMATION: Synthetic peptide

<400> SEQUENCE: 12

Lys Tyr Gly Arg Asp Phe Leu Leu Arg Phe Arg Tyr Ile Arg Ser
1               5                   10                  15

<210> SEQ ID NO 13
<211> LENGTH: 17
<212> TYPE: PRT
<213> ORGANISM: Artificial
<220> FEATURE:
<223> OTHER INFORMATION: Synthetic peptide

<400> SEQUENCE: 13

Lys Lys Lys Tyr Gly Arg Asp Phe Leu Leu Arg Phe Arg Tyr Ile Arg
1               5                   10                  15
Ser

<210> SEQ ID NO 14
<211> LENGTH: 17
<212> TYPE: PRT
<213> ORGANISM: Artificial
<220> FEATURE:
<223> OTHER INFORMATION: Synthetic peptide

<400> SEQUENCE: 14

Gly Gly Lys Tyr Gly Arg Asp Phe Leu Leu Arg Phe Arg Tyr Ile Arg
1               5                   10                  15
Ser

<210> SEQ ID NO 15
<211> LENGTH: 17
<212> TYPE: PRT
<213> ORGANISM: Artificial
<220> FEATURE:
<223> OTHER INFORMATION: Synthetic peptide

<400> SEQUENCE: 15

Arg Arg Arg Tyr Gly Arg Asp Phe Leu Leu Arg Phe Arg Tyr Ile Arg
1               5                   10                  15
Ser

<210> SEQ ID NO 16
<211> LENGTH: 17
<212> TYPE: PRT
<213> ORGANISM: Artificial
<220> FEATURE:
<223> OTHER INFORMATION: Synthetic peptide

<400> SEQUENCE: 16

Arg Arg Lys Tyr Ala Arg Asp Phe Leu Leu Arg Phe Arg Tyr Ile Arg
1               5                   10                  15
Ser

<210> SEQ ID NO 17
<211> LENGTH: 17
<212> TYPE: PRT
<213> ORGANISM: Artificial
<220> FEATURE:
<223> OTHER INFORMATION: Synthetic peptide

<400> SEQUENCE: 17

Arg Arg Lys Tyr Ser Arg Asp Phe Leu Leu Arg Phe Arg Tyr Ile Arg
1               5                   10                  15

Ser

<210> SEQ ID NO 18
<211> LENGTH: 17
<212> TYPE: PRT
<213> ORGANISM: Artificial
<220> FEATURE:
<223> OTHER INFORMATION: Synthetic peptide

<400> SEQUENCE: 18

Arg Arg Lys Tyr Gly Lys Asp Phe Leu Leu Arg Phe Arg Tyr Ile Arg
1               5                   10                  15

Ser

<210> SEQ ID NO 19
<211> LENGTH: 17
<212> TYPE: PRT
<213> ORGANISM: Artificial
<220> FEATURE:
<223> OTHER INFORMATION: Synthetic peptide

<400> SEQUENCE: 19

Arg Arg Lys Tyr Gly His Asp Phe Leu Leu Arg Phe Arg Tyr Ile Arg
1               5                   10                  15

Ser

<210> SEQ ID NO 20
<211> LENGTH: 17
<212> TYPE: PRT
<213> ORGANISM: Artificial
<220> FEATURE:
<223> OTHER INFORMATION: Synthetic peptide

<400> SEQUENCE: 20

Arg Arg Lys Tyr Gly Arg Glu Phe Leu Leu Arg Phe Arg Tyr Ile Arg
1               5                   10                  15

Ser

<210> SEQ ID NO 21
<211> LENGTH: 17
<212> TYPE: PRT
<213> ORGANISM: Artificial
<220> FEATURE:
<223> OTHER INFORMATION: Synthetic peptide

<400> SEQUENCE: 21

Arg Arg Lys Tyr Gly Arg Ala Phe Leu Leu Arg Phe Arg Tyr Ile Arg
1               5                   10                  15

Ser

<210> SEQ ID NO 22
<211> LENGTH: 17

```
<212> TYPE: PRT
<213> ORGANISM: Artificial
<220> FEATURE:
<223> OTHER INFORMATION: Synthetic peptide

<400> SEQUENCE: 22

Arg Arg Lys Tyr Gly Arg Asp Phe Leu Leu Arg Lys Arg Tyr Ile Arg
1               5                   10                  15
Ser

<210> SEQ ID NO 23
<211> LENGTH: 17
<212> TYPE: PRT
<213> ORGANISM: Artificial
<220> FEATURE:
<223> OTHER INFORMATION: Synthetic peptide

<400> SEQUENCE: 23

Arg Arg Lys Tyr Gly Arg Asp Phe Leu Leu Arg Trp Arg Tyr Ile Arg
1               5                   10                  15
Ser

<210> SEQ ID NO 24
<211> LENGTH: 17
<212> TYPE: PRT
<213> ORGANISM: Artificial
<220> FEATURE:
<223> OTHER INFORMATION: Synthetic peptide

<400> SEQUENCE: 24

Arg Ile Lys Tyr Asp Arg Lys Phe Leu Leu Asp Arg Lys Tyr Ile Arg
1               5                   10                  15
Ser

<210> SEQ ID NO 25
<211> LENGTH: 7
<212> TYPE: PRT
<213> ORGANISM: Artificial
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: can be replaced with any other amino acid
<220> FEATURE:
<221> NAME/KEY: VARIANT
<222> LOCATION: (3)..(3)
<223> OTHER INFORMATION: can be replaced with any other amino acid
<220> FEATURE:
<221> NAME/KEY: VARIANT
<222> LOCATION: (4)..(4)
<223> OTHER INFORMATION: can be replaced with any other amino acid
<220> FEATURE:
<221> NAME/KEY: VARIANT
<222> LOCATION: (5)..(5)
<223> OTHER INFORMATION: can be replaced with any other amino acid
<220> FEATURE:
<221> NAME/KEY: VARIANT
<222> LOCATION: (7)..(7)
<223> OTHER INFORMATION: can be replaced with = "Met" or "Phe"

<400> SEQUENCE: 25

Tyr Gly Arg Asp Phe Leu Leu
1               5

<210> SEQ ID NO 26
<211> LENGTH: 54
<212> TYPE: DNA
```

```
<213> ORGANISM: Artificial
<220> FEATURE:
<223> OTHER INFORMATION: primer

<400> SEQUENCE: 26
taattgctag cttaatacga ctcactatag ggaccggtcg ccaccatggt gagc        54

<210> SEQ ID NO 27
<211> LENGTH: 34
<212> TYPE: DNA
<213> ORGANISM: Artificial
<220> FEATURE:
<223> OTHER INFORMATION: primer

<400> SEQUENCE: 27
ttattgaatt cacttgtaca gctcgtccat gccg                              34

<210> SEQ ID NO 28
<211> LENGTH: 88
<212> TYPE: DNA
<213> ORGANISM: Artificial
<220> FEATURE:
<223> OTHER INFORMATION: primer

<400> SEQUENCE: 28
ttattgaatt caagcgatgc tgcagaagcg gaaacgtagc aggaagtctc ggccatactt  60
gcgtctcttg tacagctcgt ccatgccg                                    88

<210> SEQ ID NO 29
<211> LENGTH: 42
<212> TYPE: DNA
<213> ORGANISM: Artificial
<220> FEATURE:
<223> OTHER INFORMATION: primer

<400> SEQUENCE: 29
gctgtacaag agacgcaagg ctggccgaga cttcctgcta cg                    42

<210> SEQ ID NO 30
<211> LENGTH: 17
<212> TYPE: PRT
<213> ORGANISM: Artificial
<220> FEATURE:
<223> OTHER INFORMATION: Synthetic peptide

<400> SEQUENCE: 30

Arg Arg Lys Tyr Ala Arg Ala Phe Leu Leu Arg Phe Arg Tyr Ile Arg
1               5                   10                  15

Ser
```

PEPTIDES USED FOR TREATING CANCERS AND, IN PARTICULAR, CHRONIC LYMPHOID LEUKAEMIA

RELATED APPLICATIONS

The present application is a U.S. National Phase Application of International Application No. PCT/FR2010/000191 (filed Mar. 5, 2010) which claims priority to French Application No. 0901007 (filed Mar. 5, 2009) which are hereby incorporated by reference in their entirety.

SEQUENCE LISTING SUBMISSION VIA EFS-WEB

A computer readable text file, entitled "045636-5173_SequenceListing.txt," created on or about Nov. 11, 2011, with a file size of about 9 kb contains the sequence listing for this application and is hereby incorporated by reference in its entirety.

Chronic lymphoid leukemia (CLL) is a hemopathy defined by the accumulation of a clone of small B lymphocytes in the blood (lymphocytes greater than $4 \times 10^9$/liter) and the bone marrow. CLL is the most common type of hemopathy in adults in the western hemisphere (O'Brien et al., 1995). It represents a third of all leukemias. Its incidence reaches 2.7 per $10^5$ individuals in the United States and in Europe. This incidence reaches 20 per $10^5$ for elderly individuals over the age of 70. The discovery of the disease is fortuitous in the majority of cases, on the occasion of a hemogram in an adult in apparent good health, leading to the discovery of a variable hyperlymphocytosis, usually between 5 and 50 000/mm³ and sometimes reaching hundreds of thousands of B lymphocytes. These B lymphocytes have particular characteristics which make it possible to distinguish them from normal B lymphocytes.

The B lymphocytes in CLL express immunoglobulins at their surface with monotypic light chains (Preud'homme and Seligmann, 1972) and idiotypic heavy chain determinants (Fu et al., 1975), reflecting the monoclonal nature of the cell. The monoclonality is confirmed by studying the immunoglobulin gene rearrangement (Fialkow et al., 1978).

CLLs are characterized by a virtually constant expression of the CD5 marker (Boumsell et al., 1978). The CD5 marker is usually present on mature T cells and is expressed in a subpopulation of normal B cells. These phenotypic characteristics today constitute one of the diagnostic criteria for the disease (Moreau et al., 1997).

The diagnosis is based on the presence of an excessive lymphocytosis observed on several hemograms with a particular morphological appearance; the immunological study confirms the increase in a population of CD19+ CD5+ CD23+ monoclonal B lymphocytes (Caligaris-Cappio and Hamblin, 1999).

The proliferative activity of the B lymphocytes in CLL is low. This is because, as observation of the expression of the cell cycle regulators shows, the cells are blocked in the G0/G1 phase of the cell cycle (Delmer et al., 1995). The clonal accumulation of these cells is linked to a defect in a mechanism of programmed cell death (PCD) called apoptosis.

The p27 protein is a proliferation inhibitor, the weak expression of which is often associated with a poor prognosis in the case of a proliferative tumor. On the other hand, for CLL, which is not a proliferative tumor, it is the overexpression of p27 which is an unfavorable prognostic factor, and could influence apoptosis processes (Vrhovac et al., 1998).

eIF4E (eukaryotic Initiation Factor 4E) is a determining factor in the control of cap-dependent translation initiation. eIF4E binds to mRNAs which have a cap at the 5' end, and associates with eIF4G so as to stimulate protein synthesis. Competitive inhibition of this interaction by the association of eIF4E with 4EBP (eIF4E Binding Protein) is a mechanism of regulation of translation initiation that is essential, in particular in the sea urchin ovule. It has been demonstrated in the sea urchin that the increase in translational activity at fertilization involves a dissociation of the eIF4E-4EBP complex and the degradation of 4E-BP (Cormier et al., 2003). The translation of specific mRNAs can also be regulated by proteins that interact both with eIF4E and with the mRNA (for overview see (Richter and Sonenberg, 2005)).

The role of eIF4E in the regulation of mRNA expression is not limited to translation initiation. The binding of the eIF4E to the cap of mRNAs protects them against exonucleolytic degradation. The interaction of eIF4E with its partners induces conformational modifications, thereby changing its affinity for the cap, and can result in degradation of the mRNA. The interaction of eIF4E with 4E-T is implicated in the cell trafficking of mRNAs to sites of storage and of degradation.

The eIF4E and 4EBP proteins are involved in survival and apoptosis mechanisms: eIF4E is characterized as being anti-apoptotic and, conversely, 4-EBP is identified as pro-apoptotic (Holcik and Sonenberg, 2005; Morley et al., 2005).

Recently, a new function has been described: eIF4E regulates the nucleocytoplasmic export of mRNA comprising a 4E-SE (4E sensitivity element) sequence. Some mRNAs comprising this sequence encode proteins involved in regulation of the cell cycle, which casts new light on the proliferative and oncogenic properties of eIF4E. This function of eIF4E requires its interaction with various partners, including homeo-domain proteins such as HoxA9 (Culjkovic et al., 2005; Topisirovic et al., 2005).

The translation of the majority of mRNAs encoding proteins involved in cell growth and proliferation is strongly dependent on the availability of eIF4E to form a functional complex with eIF4G in the cell (Koromilas et al., 1992). 4EBP negatively regulates this interaction by associating with eIF4E. With the aim of mimicking the function of 4EBP, synthetic peptides or molecules capable of binding to eIF4E have been sought (Herbert et al., 2000; Moerke et al., 2007).

A library of chemical compounds was screened with regard to the eIF4E-binding property of these compounds (Moerke et al., 2007). One compound selected, 4EGI-1, is capable of inhibiting the translation of proteins involved in cell growth and proliferation, this effect being greater in cells which overexpress the bcr-abl oncogene. Furthermore, 4EGI-1 causes an increase in the proportion of DNA in sub-G0/G1, and the appearance of an apoptotic-type nuclear morphology. 4EG-1 is no longer active in the presence of ZVAD.fmk, an inhibitor of apoptosis. 4-EGI-1 therefore leads to a PCD of apoptotic type. Since these experiments were carried out on cells in the presence of serum, the effect of 4EGI-1 is therefore exerted on proliferating cells, and involves the "conventional" apoptosis pathway.

The introduction of peptides based on the binding motif for 4EBP and eIF4G into MRC5 cells, cultured without serum for 72 hours, results in rapid cell death (Herbert et al., 2000). This cell death is similar to a PCD, firstly by virtue of the characteristics of the DNA of the treated cells (fragmentation observed by immunofluorescence, sub-G0/G1 profile by FACS) and, secondly, by virtue of a modification of mitochondrial permeability. This PCD is not "conventional" apoptosis since it is independent of caspase activation and is not inhibited by the apoptosis inhibitor ZVAD-.fmk. Furthermore, this cell death is translation-independent since the effect of the peptides endures after treatment of the cells with translation inhibitors. Contrary to the Moerke study (above), the effect of the peptides is exerted on cells cultured without serum, and therefore on cells arrested in G0/G1, and via a mechanism of PCD other than "conventional" apoptosis.

In this context, the inventors have evaluated the ability of peptides that can interact with eIF4E, and that are known or have been identified by an original functional genomic approach, to induce CLL lymphocyte cell death. They have thus demonstrated that, unlike the peptides described in the prior art for their ability to bind to eIF4E, the A1 WT IRS peptide, of sequence RRKYGRDFLLRFRYIRS (SEQ ID No. 2), when it is incubated with B lymphocytes derived from patients suffering from CLL and placed in culture, causes a high mortality of these lymphocytes. This effect is essentially early during the incubation with the cells in culture, and has an advantageous specificity with respect to the myeloid and lymphoid cell lines. Thus, particularly advantageously, the peptide of the invention causes cell death of lymphocyte lines as early as 15 minutes after the peptide has been brought into contact with the cells, which makes it a particularly fast-acting compound compared with the prior art compounds known to induce cell death. Such a fast action makes it possible to envision a limitation of the mechanisms of resistance which can be induced in the body in response to a therapeutic treatment using slower-acting compounds.

The inventors have also been able to demonstrate that the cell-death-inducing effects of the A1 WT peptide can be extended to cell lines derived from solid tumors.

The A1 WT IRS peptide corresponds to a sequence derived from the human Angel 1 protein (A1 WT peptide of sequence RRKYGRDFLLRF (SEQ ID No. 3)), fused, at its C-terminal end, to a sequence which promotes its entry into cells. The inventors have put forward the hypothesis that this peptide can retain its activity despite several substitutions in its sequence, thus determining a generic sequence of peptides that are active in this context.

The invention therefore relates, firstly, to a peptide comprising the sequence $X_1X_2X_3YX_4X_5X_6X_7LX_8X_9X_{10}$ (SEQ ID No. 1), in which:

$X_1$ and $X_2$ represent, independently of one another, an amino acid chosen from R, K and H, with preferably $X_1=X_2=R$;

$X_3$ represents an amino acid chosen from R, K and H, preferably R or K;

$X_4$, $X_5$ and $X_6$ represent any amino acid, with preferably:
$X_4$=G, A or S, more preferentially A or S, and/or
$X_5$=R or H, more preferentially R, and/or
$X_6$=D, E, A, V, L, P, M, F, I or X, more preferentially D or A;

$X_7$ represents an amino acid chosen from F, A, V, L, I and M, preferably F;

$X_8$ represents an amino acid chosen from L, M and F, preferably L;

$X_9$ represents any amino acid, preferably R;

$X_{10}$ represents an amino acid chosen from F, Y, W and H, preferably F or W, for treating a cancer, in particular a solid-tumor or liquid-tumor cancer, and more particularly for treating a malignant hematopoietic disease.

The peptide according to the invention will be particularly effective for treating a leukemia or a lymphoma, and in particular chronic lymphoid leukemia (CLL), B-cell prolymphocytic leukemia (B-PLL), T-cell acute lymphoblastic leukemia (T-ALL), marginal zone lymphoma (MZL), mantle cell lymphoma and acute myeloid leukemia (AML). The peptide according to the invention may also be of use for treating cervical cancer.

In the present text, the term "peptide" denotes any molecule of which the core consists of amino acids, in L or D configuration, which can optionally be replaced with amino acids that have been modified so as to have better pharmocokinetic properties, such as N-methylated α-amino acids or constrained (optionally non-proteinogenic) amino acids (Cowell et al., 2004). In a peptide for the purpose of the present invention, the amino acids or analogs thereof can be connected to one another by peptide bonds (—CO—NH—), but the term "peptide" also denotes any series of amino acids (or analogs) in which one or more peptide bonds has (have) been modified, in particular in order to increase the resistance of the molecule to proteolysis. Where appropriate, other chemical groups can be covalently bonded to this peptide, in order to provide it with better stability, to protect it in vivo and/or to give it additional properties, for example in order to promote its entry into cells, and/or to promote its targeting to the cells to be treated (in the case of CLL, the B lymphocytes).

By way of examples of groups capable of being bonded to the peptide of the invention in order to improve its stability and/or to slow down its destruction or its elimination in vivo, mention may be made of cysteamide, cysteine, thiol, amide, carboxyl, linear or branched $C_1$-$C_6$ alkyl, substituted alkyl, primary or secondary amine, saccharide derivative, lipid, phospholipid, fatty acid, cholesterol, polyethylene glycol, acetyl, etc. groups. Those skilled in the art may choose to graft one or more of these groups at the N- and/or C-terminal ends of the peptide. If necessary, for example in the case of an N-terminal addition of cholesterol, a peptide bridge will be used to bond a nonpeptide molecule to the peptide of the invention. An example of a bridge that can be used for this is the -CA$_β$-bridge.

Another means, widely illustrated by the scientific literature, of obtaining protection and stabilization of the peptides in vivo is to cyclize them. Where appropriate, a peptide bridge or nonpeptide bridge (for example S—S or C—C) is added between the N- and C-terminal ends of the linear peptide, in order to provide cyclization thereof. According to one preferred embodiment of the invention, the peptide comprising the sequence SEQ ID No. 1 is cyclized.

By way of examples of groups that promote entry of the peptide of the invention into cells, mention may be made of certain peptide sequences, for example the "penetratin" sequences, such as the IRS sequence composed of the RYIRS amino acid sequence (SEQ ID NO. 4) (used in the experimental section presented below), or the sequence KKWKMRRNQFWVKVQRG (Kanovsky et al., 2001). Such a sequence will preferably be bonded to the C-terminal end of the peptide of the invention, by a peptide bond or the like. Other components capable of promoting entry of the peptide into the cell can be used, for instance nanoparticles.

By way of examples of groups that promote targeting of the peptide to certain cell types, mention may, of course, be made of peptide compounds such as immunoglobulins, in particular antibodies, and also epitopes or fragments of antibodies (Fab) which specifically target cell surface elements (antigens, receptors) of the targeted cellular type, etc., but also sugars, such as monosaccharides (for example: glucose, galactose, glucosamine or galactosamine), oligosaccharides, polysaccharides, or analogs thereof, and also certain oligonucleotides, or certain organic molecules such as folate. The targeting function of such molecules is linked to the fact that they constitute ligands of certain receptors overexpressed at the cell surface of the cells of interest.

In particular, the targeting of the peptide to the CLL B lymphocytes can be provided (i) by bonding to a targeting peptide such as the IRS sequence mentioned above; (ii) by bonding of the peptide to a carbohydrate structure such as Sia-α2-6 Gal-β1-4G1cNAc (Hanasaki et al., 1995), which targets the CD22 molecule of B lymphocytes; and/or (iii) by incorporation of the peptide in immuno-nanoparticles coated with a specific antibody which recognizes one or more antigen(s) of B lymphocytes (for example: CD5 and HLA-DR or CD5-Fc γ RuB).

It should be noted that the IRS sequence may:
either be conserved,
or be replaced with another targeting peptide which recognizes an endocytosis receptor on the CLL B lymphocyte (for example: HLA-DR),
or be deleted if the peptide is bonded to a carbohydrate structure or if the peptide is incorporated into an immuno-nanoparticle.

The targeting strategies may also promote entry of the peptide into cells.

It is important to note that although some of the components which can be bonded to the peptide of SEQ ID No. 1 comprise amino acids, the invention does not relate to any peptide or protein comprising this sequence, independently of the amino acids located around the sequence SEQ ID No. 1. Specifically, the only peptide sequences which can be bonded to the peptide of the invention are, as described above, peptide bridges (the length of which will not exceed 5 amino acids), peptides promoting entry into cells (the length of which will not exceed 20 to 25 amino acids, preferably 5 to 17 amino acids), and targeting peptides (the size of which will not exceed 50 amino acids, preferably 5 to 20 amino acids). A peptide according to the invention therefore has structural characteristics (presence of SEQ ID No. 1; size not exceeding 75 amino acids approximately, preferably less than 20 amino acids), but also functional characteristics, since it must retain the activity of the A1 IRS peptide of SEQ ID No. 2, as described in example 4 below, where appropriate combined with additional functionalities such as the targeting of certain cell types, in particular B lymphocytes.

According to one preferred embodiment of the invention, the peptide used for treating a disease such as chronic lymphoid leukemia is the A1 WT IRS peptide of sequence RRKYGRDFLLRFRYIRS (SEQ ID No. 2).

The invention also relates to a pharmaceutical composition, intended in particular for treating chronic lymphoid leukemia, and comprising a peptide as described above, associated with a vector. There is a very abundant literature on the vectors that can be used to deliver peptide compounds into cells, and those skilled in the art are free, in order to implement the invention, to use a peptide of sequence SEQ ID No. 1 in combination with any component capable of promoting its stability, its entry into cells and/or its targeting. By way of nonlimiting examples of vectors which can be used to deliver the peptide of the invention, mention may be made of those described in the articles by (Deshayes et al., 2008; Foged and Nielsen, 2008; Malik et al., 2007) and (Soares et al., 2007). Moreover, the vector may be an immunoglobulin, in particular an antibody.

In addition to the aforementioned arrangements, the invention also comprises other arrangements, which will emerge from the experimental examples below and from the appended figures.

FIGURE LEGENDS

FIG. 1: Test for interaction of the peptide sequences with eIF4E

The eIF4E protein fused to glutathione-S-transferase (GST-eIF4E) or GST alone (GST), used as a control, are produced in bacteria, purified and immobilized on glutathione beads. The YFP, YFP-A1 WT and YFP-A1 YALA proteins were produced in rabbit reticulocyte lysate in the presence of 35S methionine and chromatographed on the GST-eIF4 or GST beads. The proteins retained on the beads are eluted and analyzed by SDS-PAGE followed by autoradiography.

One tenth of the YFP, YFP-A1 WT and YFP-A1 YALA proteins used per assay were loaded onto the gel (input 1/10, lane 1, 4, 7).

Figure 2:
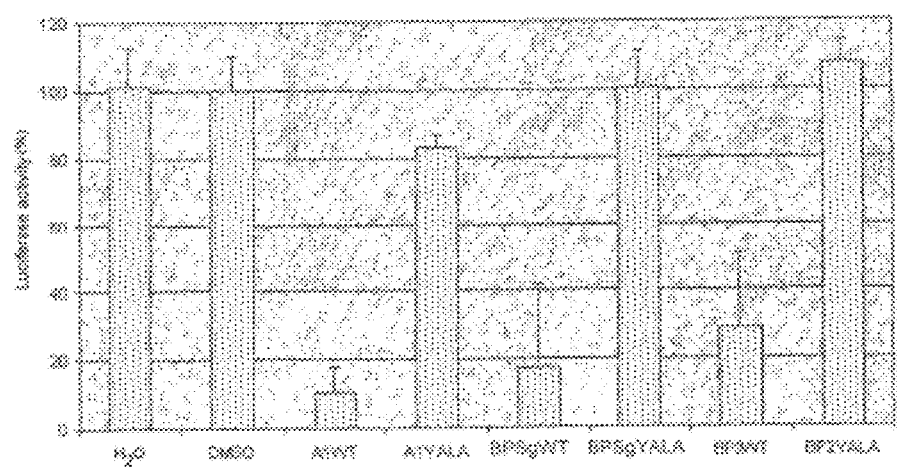

FIG. 2: Effect of the peptides on translation

The peptides having the IRS motif and the sequences of 4EBPlike type (A1WT, BPSgWT, and BP2WT) or the mutant sequences of 4EPBlike type (A1YALA, BPSg-YALA, BP2YALA) are incubated in rabbit reticulocyte lysate containing capped mRNAs encoding luciferase, an enzyme of which the activity can be easily assayed. The translational activity is directly proportional to the activity of the luciferase produced. The translational activity in the presence of peptide is compared with that obtained during the addition of an equivalent volume of DMSO, considered to be 100%.

Figure 3:
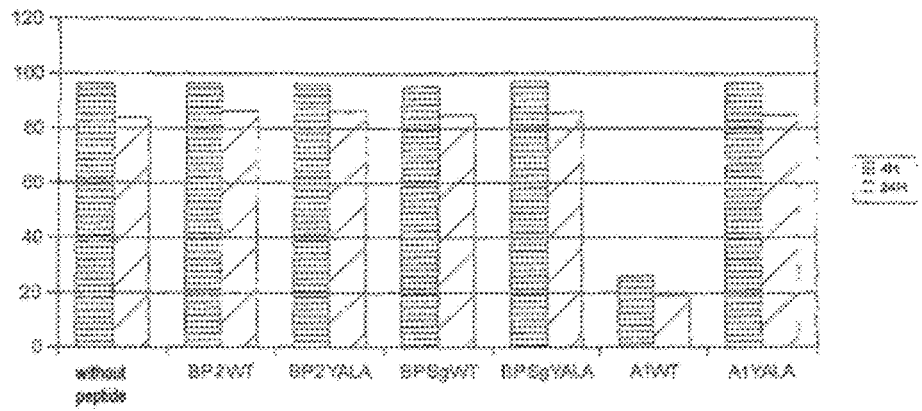

FIG. 3: Effect of the peptides on cell survival

Peripheral blood B lymphocytes taken from patients suffering from CLL and then purified on a Ficoll cushion and placed in culture are incubated in the presence of 40 μm of the peptides described for FIG. 2. The percentage cell survival after 4 hours (gray column) or 24 hours (white column) of culture corresponds to the percentage of cells labeled neither with annexin nor with propidium iodide, evaluated by flow cytometry.

Figure 4:
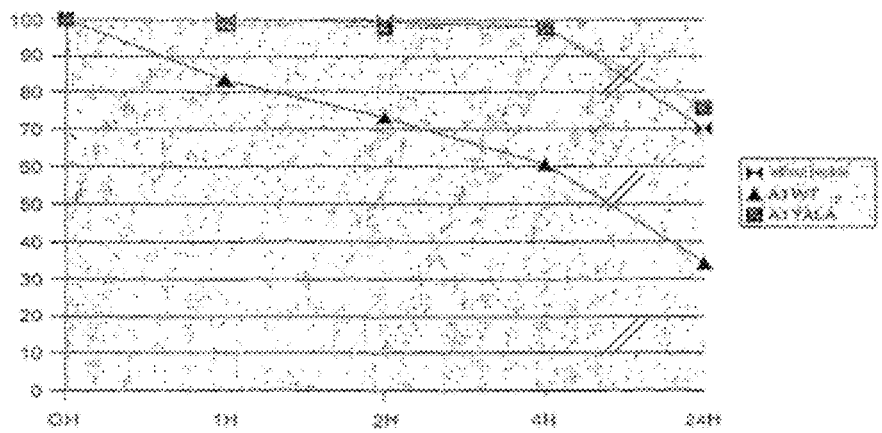

FIG. 4: Effect of the peptides on cell survival after various incubation times:

The cells are treated as indicated for FIG. 3, except that the percentage cell survival is evaluated after various incubation times: 1 H, 2 H, 4 H and 24 H.

Figure 5:
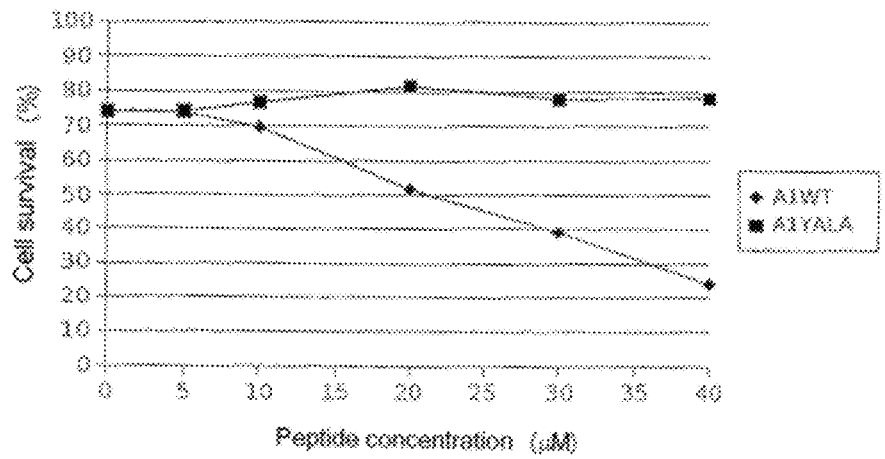

FIG. 5: Dose-dependent effect of the A1 WT peptide on cell survival

The cells are treated as indicated in FIG. 3, with a peptide concentration of 0, 5, 10, 20, 30 or 40 μm. The cell survival is determined after 24 H of culture in the presence of peptide.

Figure 6:
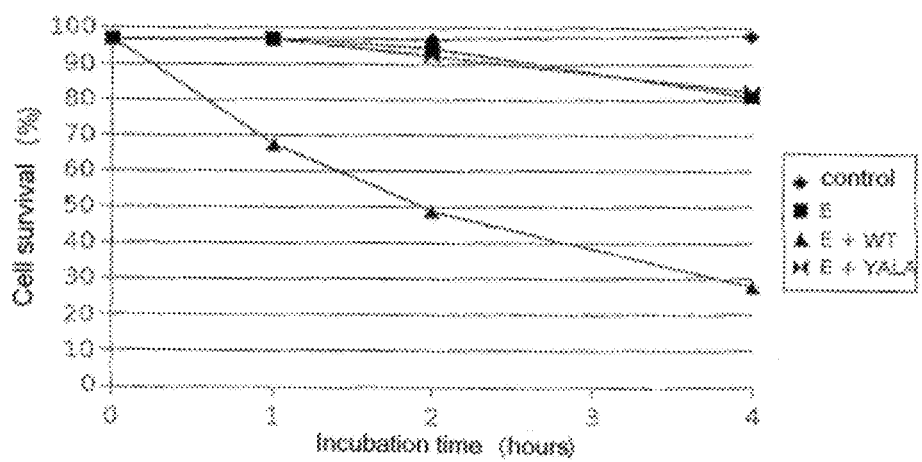

FIG. 6: Activity of the A1WT peptide in the presence of emetine

The cells are prepared and placed in culture as indicated for FIG. 3. The cells are preincubated for one hour with 100 μM of emetine before the addition of 40 μM of the A1WT or A1YALA peptides. The percentage cell survival is evaluated after 1 H, 2 H and 4 H of incubation.

Figure 7:
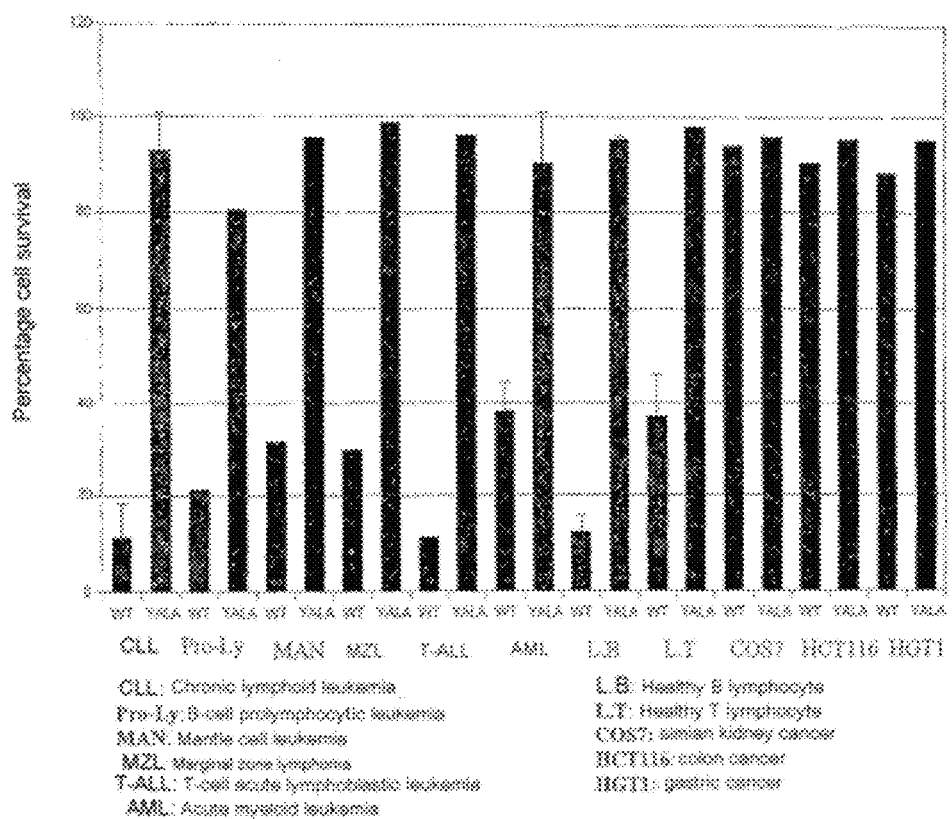
Figure 5A:
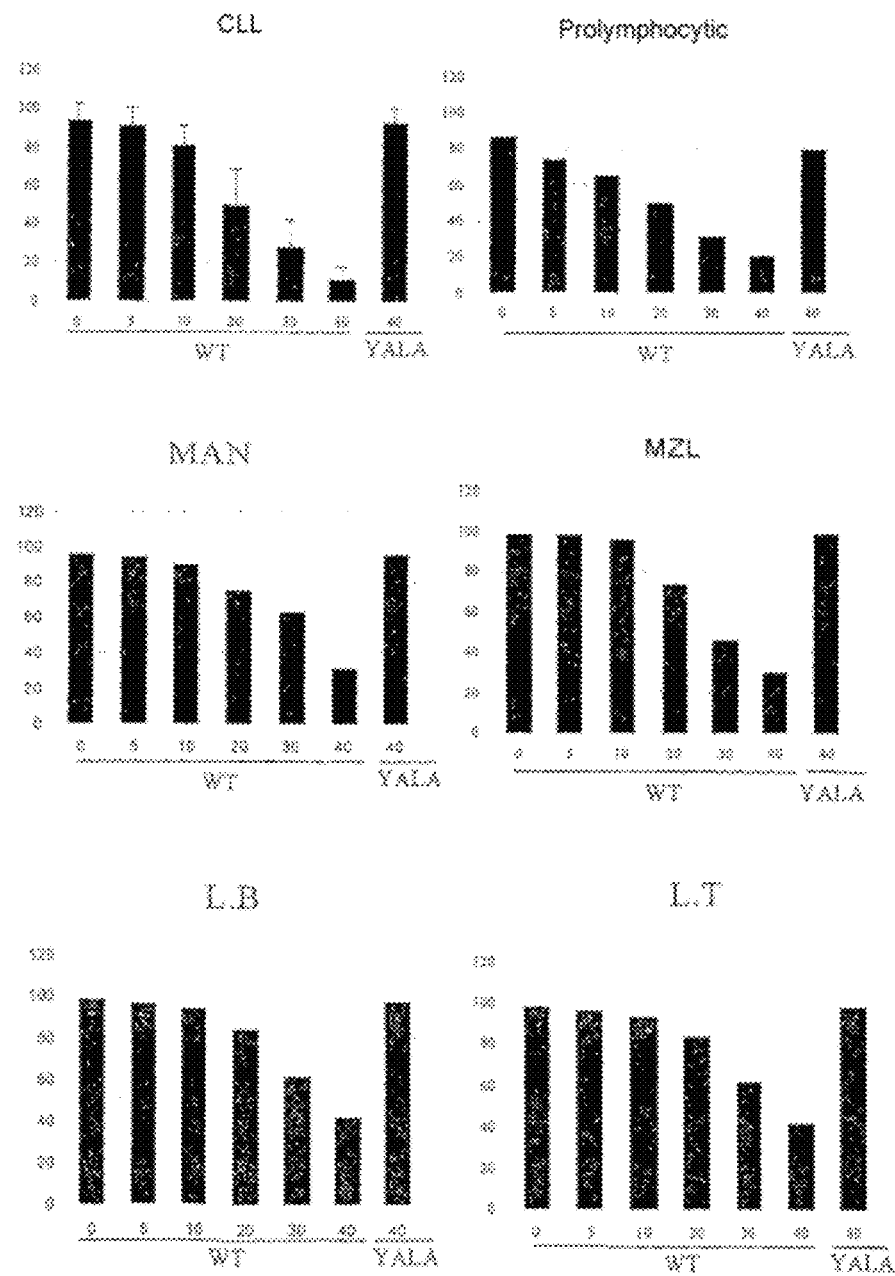

FIG. 7: Activity of the A1WT peptide on cells of lymphocytic, lymphoid, gastric, colonic or renal origin The cells are prepared and placed in culture (see Materials and Methods) and then incubated for 4 H with the A1WT or A1 YALA peptide. The percentage cell survival corresponds to the percentage of cells labeled neither with annexin nor with propidium iodide, evaluated by flow cytometry. The names of the pathological conditions from which the patients from whom the samples are taken are suffering are indicated under the figure. The control T (L.T.) and B (L.B.) lymphocytes are taken from patients suffering from a disease not related to a lymphocytic pathological condition (hemochromatosis).

Figure 8:
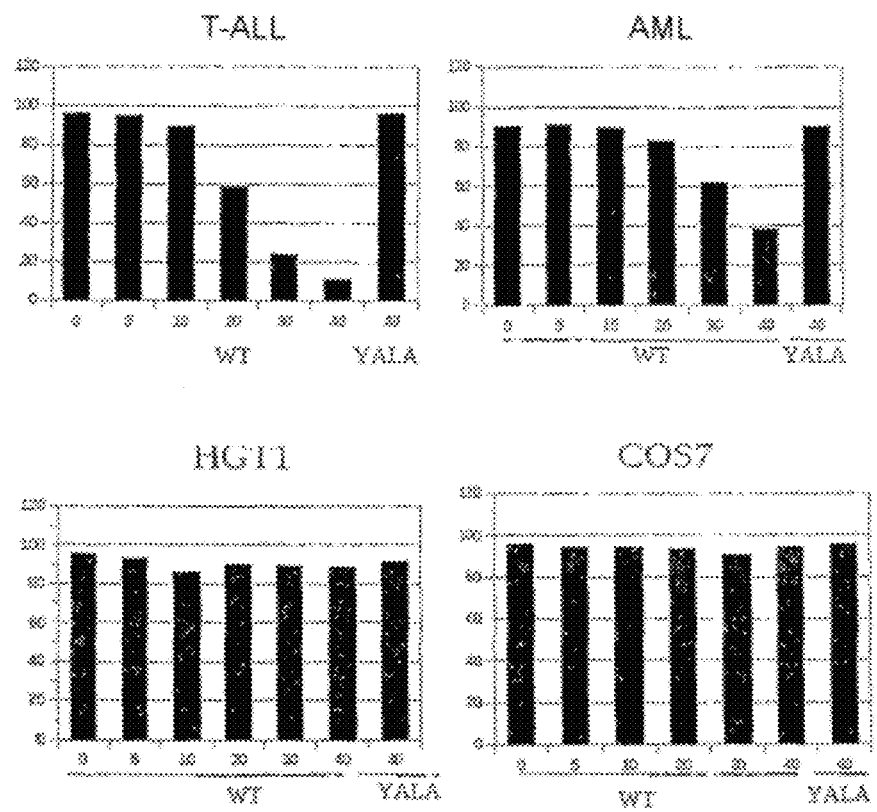

FIG. 8: Dose-dependent effect of the A1WT peptide on cells of lymphocytic, lymphoid, gastric, colonic or renal origin Panels A and B, the cells are prepared and treated as indicated for FIG. 3, except that the cells were incubated with 0, 5, 10, 20, 30 or 40 mM of A1WT peptide or 40 mM of A1 YALA peptide. The abbreviations of the names of the pathological conditions from which the patients from whom the samples were taken are suffering are indicated in FIG. 7.

Figure 9:
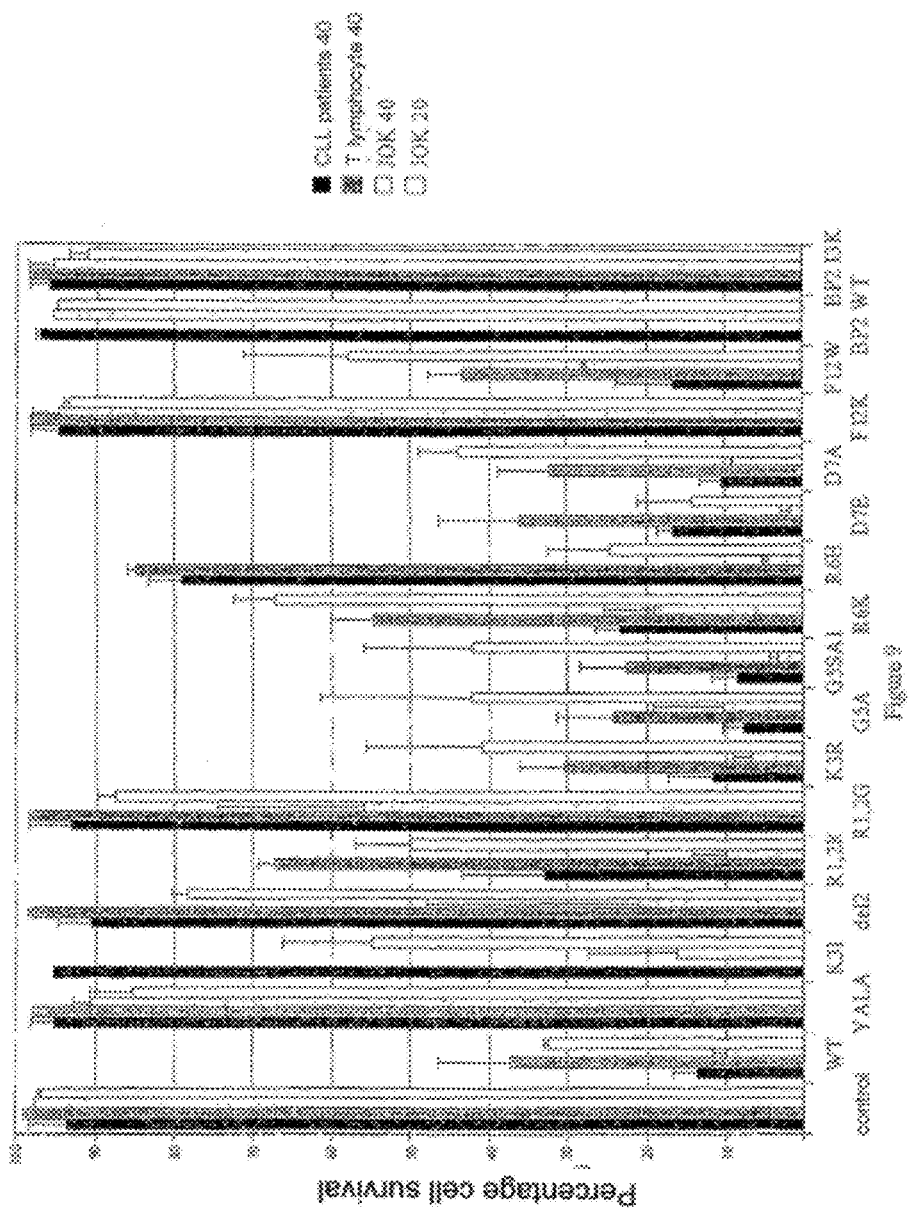

FIG. 9: Activity of the A1 WT IRS peptide and of derivatives thereof on the survival of CLL cells, control T lymphocytes and Jok lymphocytes The cells are treated as indicated for FIG. 7, with the CLL cells, control T lymphocytes and Jok lymphocytes, which are incubated with the A1 WT IRS peptide and derivatives thereof described in table 1. The Jok cells were incubated either with 20 µM (JOK 20) or with 40 µM (JOK 40) of each of the peptides. In the interests of simplifying the legend, the A1 WT IRS peptide is referred to as "WT". Likewise, the derivatives thereof are referred to by the name of the mutations (A1 K3I IRS is referred to as "K3I", for example).

Figure 10:
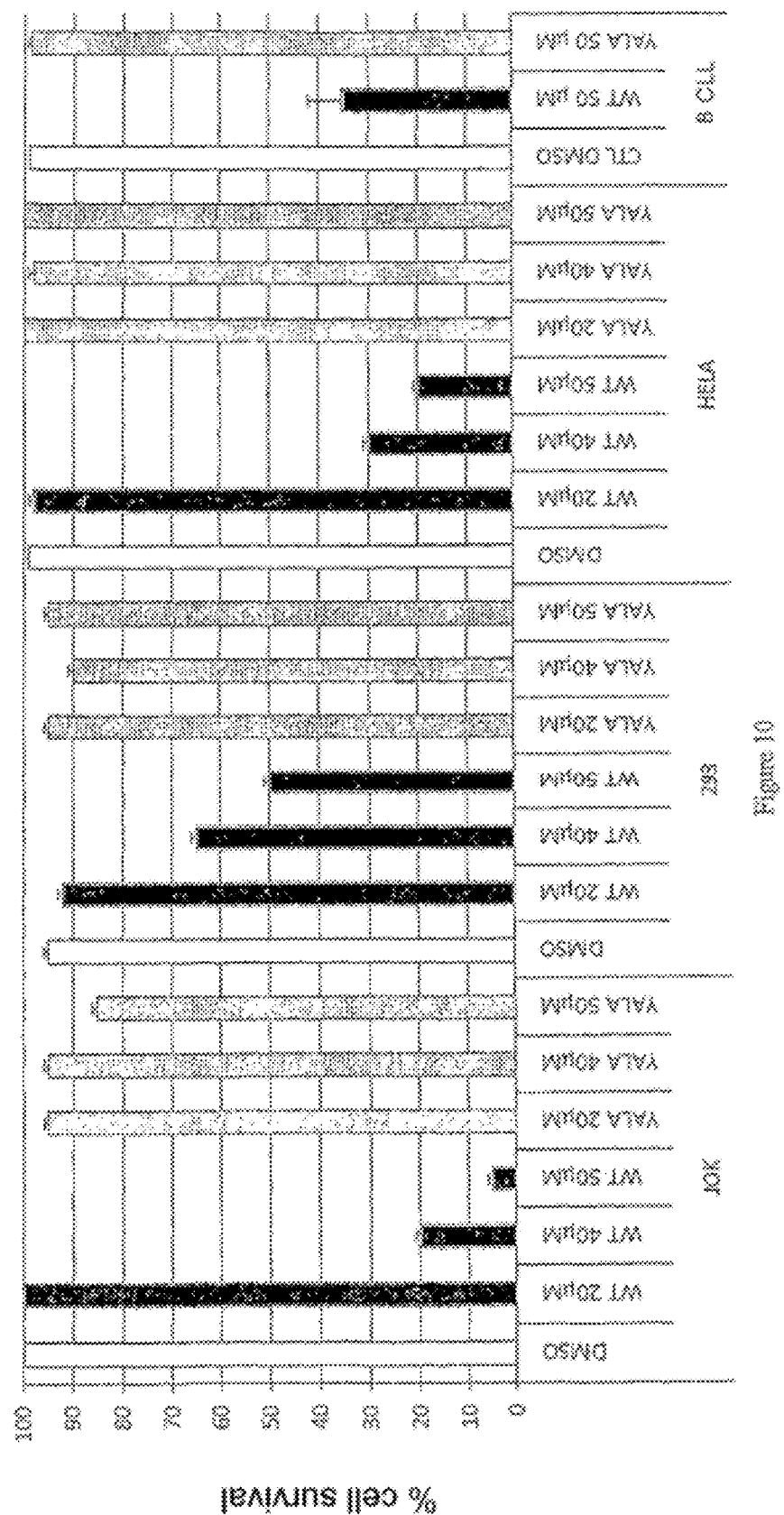

FIG. 10: Activity of the A1WT peptide on cells of lymphocytic (JOK and CLL B), renal (293) and cervical HeLa) origin The cells cultured in glass-bottomed multiwell plates are incubated for one hour with the A1WT or A1 YALA peptide at the concentrations indicated on the figure. The percentage cell survival is obtained by calculating the ratio between the cells stained with Syto 13 and those stained with propidium iodide (see Materials and Methods).

Figure 11:
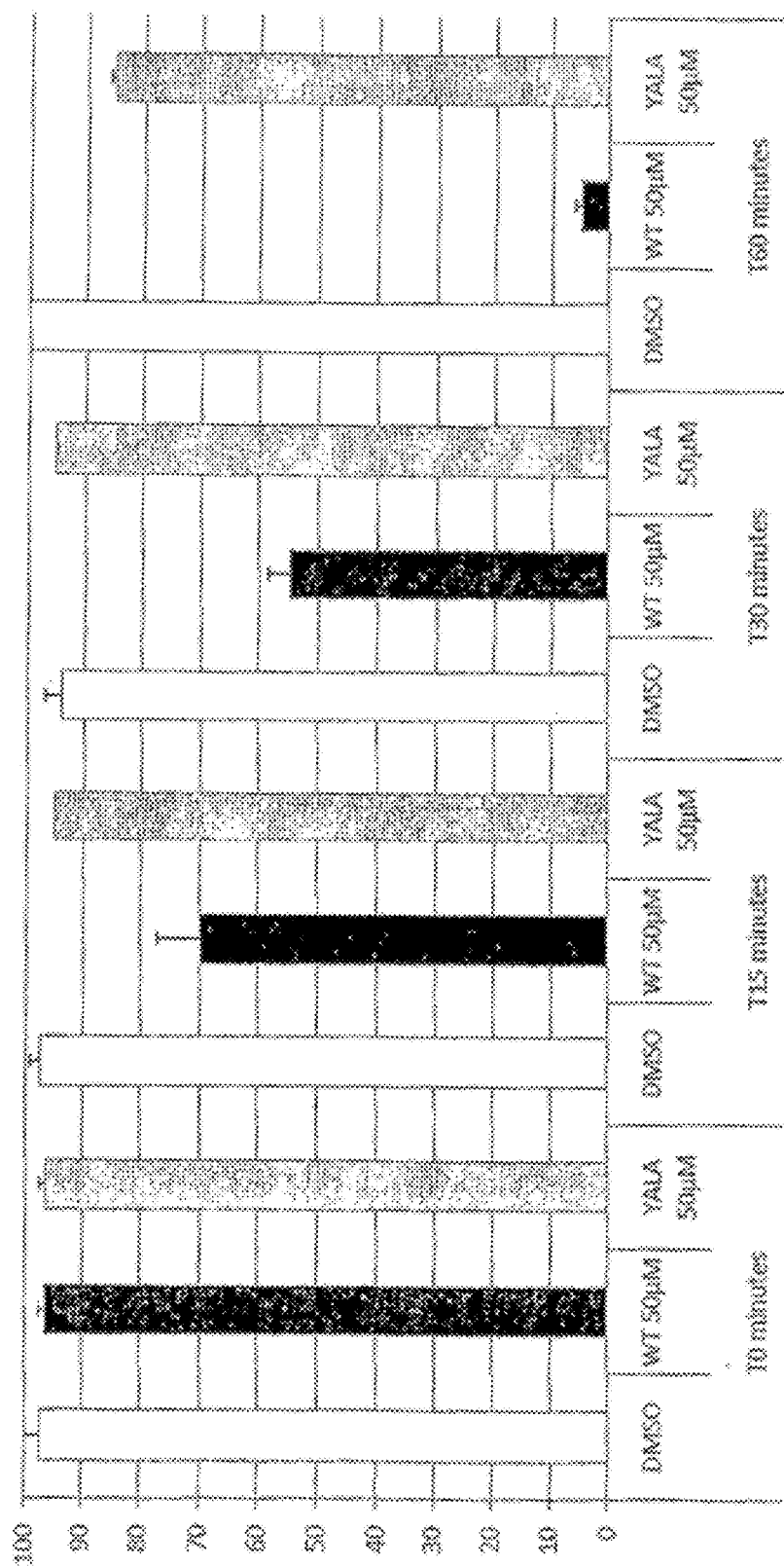

FIG. 11: The A1WT peptide causes rapid mortality of the cells of lymphocytic origin (JOK)

The cells are treated as indicated for FIG. 10, except that the incubation time in the presence of the peptide ranges from 15 min to 1 h.

EXAMPLES

The experimental examples described hereinafter were obtained using the following materials and methods:
Test for Interaction of the Peptides Fused to YFP The plasmids encoding the YFP protein-peptides were obtained by amplification of the reading frame of the YFP protein (enhanced yellow-green variant of the *Aequorea victoria* green fluorescent protein) from the pEYFP-C1 plasmid (Clontech). The 5' primer used (sequence described below) made it possible to insert a T7 promoter (underlined sequence) upstream of the reading frame of YFP. The YFP 3' primer provided the amplification of YFP, while the A1 WT 3' primer made it possible to fuse the C-terminal end of YFP to the sequence of the A1 WT peptide. The amplimers were cloned into the pCR 2.1-TOPO plasmid (TOPO TA cloning kit, Invitrogen). The mutation of YFP-A1 WT in order to obtain YFP A1 YALA was carried out using the A1 YALA mutagenesis primer. The YFP, YFP A1 WT and YFP A1 YALA proteins were produced in rabbit reticulocyte lysate (RRL) in the presence of 35S Met according to the suppliers' indications (TNT T7 coupled rabbit reticulocyte lysate system, Promega). The pGEX 4E plasmid was obtained by inserting the reading frame of the mouse eIF4E protein at the BamHI/EcoRI sites of the PGEX-4T-1 vector (Amersham pharmacia biotech). The recombinant mouse eIF4E protein N-terminally fused to GST was produced in BL21DE3 bacteria (Novagen) from the pGEX4G-eIF4E plasmid and attached to glutathione beads according to the supplier's indications (Glutathione sepharose 4B bead column, Amersham Pharmacia Biotech). 5 ml of programmed RRL were incubated in the presence of 20 ml of GST-eIF4E beads in a volume of 400 ml of PBS. After washing, the proteins were eluted with SDS loading buffer, and analyzed, after an SDS-PAGE gel, by autoradiography (Typhoon Phospholmager, Amersham Pharmacia Biotech).

```
Primer 5':
                                    (SEQ ID No: 26)
TAATTGCTAGCTTAATACGACTCACTATAGGGACCGGTCGCCACC

ATGGTGAGC

Primer 3' YFP:
                                    (SEQ ID No: 27)
TTATTGAATTCACTTGTACAGCTCGTCCATGCCG Primer 3' A1 WT:
                                    (SEQ ID No: 28)
TTATTGAATTCAAGCGATGCTGCAGAAGCGGAAACGTAGCAGGA

AGTCTCGGCCATACTTGCGTCTCTTGTACAGCTCGTCCATGCCG

A1 YALA mutagenesis primer:
                                    (SEQ ID No: 29)
GCTGTACAAGAGACGCAAGGCTGGCCGAGACTTCCTGCTACG.
```

Analysis of the Effect of the Peptides on Translation in Rabbit Reticulocyte Lysate The peptides were produced, purified by HPLC (purity>95%), and freeze-dried by Thermofisher Scientific. The peptides were then dissolved at 10 mM in DMSO.

The capped mRNAs encoding Renilla luciferase (Luc R) were produced by the T7 Message Machine Kit system (Ambion) from the pGb-Eg2-410Δ2-hxG-A65 plasmid linearized with EcoRV (Legagneux V, Omilli F, Osborne HB (1995) Substrate-specific regulation of RNA deadenylation in Xenopus embryo and activated egg extracts. RNA 1: 1001-1008).

The Luc R mRNAs were translated for one hour at 30° C. in rabbit reticulocyte lysate (Flexi Rabbit Reticulocyte Lysate System, Promega) in the presence of 50 µM of peptide. The luciferase activity was determined using the Renilla luciferase assay (Promega) on the Tristar LB941 luminometer (Berthold).

Lymphocyte Isolation

The CLL B lymphocytes were obtained from peripheral blood of 18 different patients suffering from chronic lymphoid leukemia. The patients had not received any treatment on the date the sample was taken, and showed various stages of progression (stage A, 12 patients; stage B, 3; stage C, 3) according to the Binet classification. The samples were taken in the Brest hospital center, in the hematology department. The blood samples were taken after informing the patients and obtaining their informed consent.

The control B lymphocytes and T lymphocytes originate from peripheral blood samples from patients suffering from hemochromatosis, provided by the CTS transfusion center in Brest. The B and T lymphocytes were isolated using the Rosett-Sep kit (Stemcell Technologies) according to the supplier's recommendations.

The lymphocytes, mononuclear cells, were isolated from the heparinized peripheral blood samples by Ficoll-Hypaque (LSM 1077 lymphocyte, euro-bio) centrifugation. The red blood cells were lyzed by incubation for 10 min in VersaLyse Lysing Solution (Beckman Coulter). The mononuclear cells are obtained after 2 washes in culture medium (RPMI1640, Gibco BRL).

After isolation, the purity of the B lymphocytes was analyzed by detection of the CD5 and CD19 antigens by flow cytometry (section 5).

Cell Culture

The cells were cultured in a culture medium composed either of RPMI 1640 (B lymphocytes) or of DMEM (COS7, HCT116, HGT1, 293, HeLa) containing 10% of FCS (fetal calf serum, 1% of penicillin-streptomycin and 1% of glutamine, Gibco BRL). The cells are distributed in a 24-well plate and cultured at 37° C. in a humid atmosphere under 5% $CO_2$.

400 µl of cell suspension ($1\times10^6$ cells/ml) per well were treated for 4 h or 24 h with various concentrations of peptides. The test for activity of the peptides in the presence of emetine (FIG. 6) was carried out by preincubating the cells with 100 µM of emetine for one hour before the addition of peptide.

Flow Cytometry Analysis

The analyses were carried out using the Coulter epics XL cytometer (Beckman Coulter).

Evaluation of the Purity of the CLL B Lymphocytes and of the Healthy B Lymphocytes For each flow cytometry analysis, 2 separate tubes were prepared, each containing $2\times10^5$ cells taken up in 100 µl of PBS buffer. 10 µl of anti-CD19 antibodies coupled to the fluorochrome Phycoerythrin (PE) (CD19 PE, Beckman Coulter) and of anti-CD5 antibodies coupled to the fluorochrome Phycocyanin (PC) (CD5 PC, Beckman Coulter) are added to one of the two tubes. 10 µl of nonspecific isotype antibodies coupled to the fluoro-chromes PE (IgG1PE, Beckman Coulter) and PC (IgG1PCy5, Beckman Coulter) are added to the second tube used as control. These antibodies bind surface markers other than CD5+ and CD19+. Consequently, the second tube serves as a negative control in the analysis of the data by flow cytometry. Both tubes are incubated for 10 minutes in the dark at ambient temperature. At the end of the incubation, 1 ml of PBS supplemented with 5% BSA is added and then the cells are washed as previously (centrifugation at 1200 rpm, 10 minutes, 20° C.). Following this washing, the supernatant is removed and then 500 µl of PBS-5% BSA are added to the cell pellet. $2\times10^5$ cells in 100 µl of PBS were exposed to the anti-CD5PC5 and anti-CD19PE antibodies coupled to fluorochromes for 10 minutes in the dark. The cell fluorescence is analyzed after washing with PBS.

Measurement of the Percentage Cell Survival

After the cells have been washed with PBS, they were analyzed using the Annexin V-FITC IP system according to the supplier's recommendations (Beckman Coulter).

Fluorescence Microscopy Analyses

The analyses were carried out on a Zeiss Observer Z1 epifluorescence microscope. The cells are cultured in a glass-bottomed multiwell plate, propidium iodide and Syto13 (Invitrogen) are added to the medium at a concentration of 1 mg/ml and 5 µM, respectively. The Syto 13 binds to the DNA in the nuclei of the cells which then emit a green fluorescence. When the membrane permeability is modified during the cell death process, the propidium iodide penetrates the cell and causes the appearance of a red fluorescence when it binds to the DNA of the cell nuclei. The ratio between the number of nuclei emitting a green fluorescence and the number of nuclei emitting a red fluorescence represents the fraction of live cells expressed as percentage cell survival in the figures.

Example 1: Identification of Peptides Having Strong Affinities with eIF4E

In order to identify and characterize peptides with very strong affinity for eIF4E, the inventors developed an original functional genomic approach called 3D-S, which combines structural biology and bioinformatics.

Various studies of the interaction between eIF4E and its partners showed that a common binding strategy was used. The eIF4E recognition motif is defined by Tyr-X-X-X-X-Leu-Φ (SEQ ID No: 25) (where X is variable and Φ is a hydrophobic residue, namely Leu, Met or Phe). In order to find novel eIF4E partners, proteins having this motif were searched for in a database containing proteins of numerous species: Trembl (http://www.ebi.ac.uk/trembl). A very large number of proteins contain this motif, which is incompatible with the expected number of partners for eIF4E considering its specific roles. This motif common to the known eIF4E partners is therefore minimal, but is not sufficient to define an eIF4E-binding site.

The inventors therefore took advantage of the available crystallographic structures to understand the mode of interaction of eIF4E and its partners, in order to construct a matrix for substitution of amino acids for the eIF4E-binding site. In other words, it is a question of defining an amino acid matrix encompassing all the sequences of which the 3D structure is compatible with an interaction with eIF4E.

On the basis of the 3D observation of the structures of eIF4E undergoing interaction with a peptide derived from 4E-BP or of a peptide derived from eIF4G, the effect of changing an amino acid was tested for each position of the eIF4E-binding site, over a length of 10 amino acids. This made it possible to generate an analysis matrix, called 3D-S/4EBS matrix (3D-S analysis matrix for eIF4E-binding site).

Using this amino acid matrix, novel eIF4E partners were searched for by bioinformatics. As expected, eIF4G and 4EBP were found. This made it possible to also identify 582 proteins having this sequence (out of a total of 2914826 proteins).

Among the proteins identified, false negatives may correspond to proteins which do not display the interaction site at their surface, or which are located in cell compartments without eIF4E. In order to increase the specificity of this search, the inventors put forward the hypothesis that, if the interaction of eIF4E with a partner was functionally important, the motif had to be conserved in evolution. Since the database comprises proteins from numerous species, a search of homologous proteins among the 582 proteins resulting from the first selection was carried out. This analysis of homology consisted of the alignment of the proteins in pairs and the forming of groups of proteins by taking the following parameters: the size of the alignment between 2 sequences A and B should correspond to at least 75% of the length of A, and the percentage identity should be greater than 50%.

Among the 582 proteins resulting from the first selection, 315 were classified in 66 groups. Fourteen groups were judged to be the most interesting. These groups, bringing together 152 proteins in total, consist of proteins of which more than 2 homologs have the eIF4E-binding site. One of the groups even comprises homologs derived from 10 different species. Among these 14 groups, 6 correspond to annotated proteins, represented in cDNA libraries, but for which no function has been described.

In conclusion, the 3D-S screening of the Trembl protein database (http://www.ebi.ac.uk/trembl) made it possible to select 582 proteins (having a 4EBPlike sequence) classified in 14 groups.

Biochemical validation of the peptides identified was then carried out by means of affinity chromatography approaches. The 4EBPlike sequence of the human homolog of each of the 14 groups was used to produce fusion proteins between YFP (yellow fluorescent protein) and each peptide in rabbit reticulocyte lysate (reaction medium allowing the translation of mRNA in vitro). The ability of these peptides to interact with eIF4E was then analyzed by affinity chromatography. Among the 14 proteins tested, 6 interact with eIF4E. Advantageously, a peptide called YFP-A1 WT (YFP, yellow fluorescent protein, fused to a peptide derived from the human Angel 1 protein, of sequence RRKYGRDFLLRF (SEQ ID No. 3)) associates more strongly with eIF4E than the other peptides tested.

Example 2: The A1 WT Peptide Interacts with eIF4E, the YALA Mutation Abolishes this Interaction The 4E-BPlike sequence of the wild type (WT) A1 protein fused to the YFP protein, and the YFP protein used alone as a control, were produced in rabbit reticulocyte lysate and labeled with radioactive methionine ($^{35}$S Met). The YFP-A1WT and YFP proteins were thus obtained in soluble form. Three amino acids known to be essential for the interaction with eIF4E in the human 4E-BP2 sequence are found in the 4E-BPlike sequence of the wild-type A1 protein. In order to obtain a mutant protein incapable of interacting with eIF4E that can be used as a control, these three amino acids were mutated so as to obtain the YFP-A1 YALA protein (mutation of the tyrosine (Y) and leucine (L) amino acids to alanine (A)), in which the A1 YALA peptide has the following sequence: RRKAGRDFAARF (SEQ ID NO. 5).

The proteins produced were analyzed on an SDS-PAGE gel, followed by autoradiography (FIG. 1, "input 1/10", lanes 1, 4, 7). YFP-A1 WT is retained on GST-eIF4E beads (lane 5), whereas nonfused YFP is not retained (lane 2). The GST beads do not retain any protein, demonstrating the specificity of the interaction (lane 6). When the three amino acids are mutated, the interaction is very weak (lane 8). This experiment shows the interaction between eIF4E and the 4E-BPlike sequence of the Angel 1 protein, and that this interaction is lost after YALA mutation.

Example 3: The A1WT Peptide, which has a Site of Interaction with eIF4E, Inhibits Translation The peptide corresponding to the 4E-BPlike sequence of the Angel 1 protein (A1WT) was chemically synthesized as a fusion with the IRS sequence composed of the RYIRS amino acids (SEQ ID NO. 4); for in vivo use, this sequence can either be retained, or be replaced with another penetratin sequence, with another polypeptide, such as an MHC molecule, for example HLA-DR, or with another component, such as a carbohydrate or a nanoparticle, etc. Peptides already known to interact with eIF4E, derived from the human 4E-BP2 (BP2WT) and *Sphaerichinus granularis* sea urchin 4E-BP (SgWT) proteins, were also synthesized, also fused to the IRS sequence. In addition, the tyrosine (Y) and leucine (L) amino acids, known to be essential for the interaction with eIF4E for the human 4E-BP2 protein, were replaced with alanines (A) in order to obtain the A1 YALA IRS, BP2 YALA IRS and Sg YALA IRS peptides which were used as control. The purity of the peptides, analyzed by mass spectrometry, is greater than 95%.

| | | |
|---|---|---|
| A1 YALA IRS: | RRKAGRDFAARFRYIRS | (SEQ ID No: 6) |
| BP2 WT IRS: | RIIYDRKFLLDRRYIRS | (SEQ ID No: 7) |
| BP2 YALA IRS: | RIIADRKFAADRRYIRS | (SEQ ID No: 8) |
| BPSg WT IRS: | RIIYDRHFLLNMRYIRS | (SEQ ID No: 9) |
| BPSg YALA IRS: | RIIADRHFAANMRYIRS | (SEQ ID No: 10) |

A capped mRNA (having a cap at the 5' end) encoding luciferase, a protein which can be easily assayed by measuring its activity, was translated in the presence of these various peptides in rabbit reticulocyte lysate (FIG. 2). The luciferase activity measured is directly proportional to the amount of luciferase protein produced and therefore to the cap-dependent translational activity. Since the peptides are dissolved in DMSO, it was important to test the effect of DMSO on the translation. It was observed that the addition of DMSO did not affect the translation (compare the addition of water ($H_2O$) and of DMSO, FIG. 2). The translational activity in the presence of peptide was compared with that obtained when an equal volume of DMSO is added, considered to be equal to 100%. In the presence of the BP2 WT IRS peptide at a final concentration of 50 µM, a strong inhibition of the translation was observed compared with the control. On the other hand, the BP2 YALA IRS peptide used as a negative control (it does not interact with the eIF4E), does not cause any inhibition of the translation of luciferase. The same is true for the peptides derived from the sea urchin 4E-BP sequence (BPSg WT IRS and BPSg YALA IRS). Advantageously, the peptide derived from the Angel 1 protein (A1 WT IRS) more substantially inhibits the translation, compared with the other peptides. As expected, the A1 YALA IRS peptide does not inhibit the translation, demonstrating the specificity of action of the A1 WT IRS peptide on eIF4E-dependent translation.

Example 4: Effect of the Peptides on CLL Lymphocytes Taken from Patients and then Placed in Culture The cells taken from patients suffering from chronic lymphoid leukemia were purified on a Ficoll cushion. The purity of the B lymphocytes, analyzed by detection of the CD5 and CD19 antigens by FACS, is greater than 95% in all the experiments carried out. The cells were placed in culture in RPMI medium in the presence of 10% FCS (fetal calf serum). The peptides were added directly to the culture medium. These peptides comprise the IRS sequence (the amino acid sequence of which is RYIRS) which is known to allow the penetration of peptides into B lymphocytes in culture (Dong et al., 2005). The cells were analyzed with the annexin/propidium iodide detection kit (Beckman Coulter), making it possible to demonstrate the extracellular exposure of phosphatidylserine and the appearance of membrane permeability, which are events characteristic of PCD. The cells which survive the treatment are those which are labeled neither with annexin nor with propidium iodide. The culture conditions allow the purified lymphocytes to survive since the percentage survival goes only from 96 to 84% after 4 H and 24 H of culture, respectively (FIG. 3). When the 4EBP2WT and BPSgWT peptides (known to interact with eIF4E) were incubated with the cells, the percentage survival did not decrease. On the other hand, the A1WT peptide (peptide discovered during this study) caused a high mortality since only 25% of the cells survived after 4 H of incubation. This percentage went to 19% after 24 H, indicating that the effect of the peptide is essentially early. The A1 YALA IRS peptide, which is incapable of interacting with eIF4E, has no effect, which indicates that the activity of the A1 WT IRS peptide is specific. This experiment making it possible to compare the effects of the 4EBPWT, BPSgWT and A1WT peptides was verified on 3 batches of purified cells (obtained from 3 different patients suffering from CLL), and on 2 batches of A1 peptides (purity greater than 95 and 99%, respectively, for each batch).

In order to follow the change in the effect of the A1WT peptide over the course of the 24 H of the experiment, the percentage survival during incubation with the A1 WT IRS and A1 YALA IRS peptides was analyzed at various times after incubation. The results are presented in FIG. 4. Although the effect of the A1 WT IRS peptide is observed during the first 4 hours of incubation, the difference in survival compared with the nontreated cells does not increase thereafter, which indicates that the peptide is no longer active after 4 H of incubation. This can be explained by a degradation of the peptide during the incubation in the culture medium. In conclusion, the A1 WT peptide causes a high mortality of the CLL B lymphocytes, and this effect is essentially early during the incubation with the cells in culture.

When the A1 WT IRS peptide was incubated at various concentrations with the CLL cells for 24 H, the cell mortality increased with the concentration of peptide (FIG. 5). The IC50, defined as the concentration of peptide capable of causing the death of 50% of the cells after 24 H, is approximately 28 µM. This experiment was reproduced on a batch of cells originating from a second patient, for which the IC50 came to 24 µM.

eIF4E, which is the target of the A1WT peptide, is involved in the regulation of translation initiation, but also in mRNA stability and transport. The inventors wanted to determine whether translation was necessary for the effect of the peptide (FIG. 6). The addition of emetine, which is a translation inhibitor, caused only a slight effect on the cell survival, which went from 97 to 82% after 4 H of incubation. The effectiveness of the translation inhibition was verified by incorporation of 35S methionine (result not shown). When the A1WT peptide was added in the presence of emetine, the cell survival went from 97% to 27% in 4 H, which shows that the peptide is still effective in the absence of translation. This experiment reproduced on a second batch of purified cells produced a similar result. The effect of the A1WT peptide on eIF4E does not therefore directly involve its translation-regulating functions.

Thus, among the various 4EBPlike peptides tested which interact with eIF4E, and inhibit the function of eIF4E in translation, only the A1WT peptide identified during this study causes, via its interaction with eIF4E, cell death in B lymphocytes from patients suffering from CLL. This effect is independent of translation and therefore affects a translation-independent function of eIF4E.

The A1WT peptide is therefore an original peptide that can potentially be exploited in therapy against CLL.

Example 5: Effect of the A1 Peptide on Various Cell Lines of Myeloid, Lymphoid, Gastric, Colonic or Renal Origin In order to determine whether the A1 peptide could be potentially exploitable for therapy against pathological conditions other than CLL, the inventors tested the effect of the A1 WT IRS peptide on other cells of lymphoid or myeloid origin. The A1 YALA IRS peptide is used as control.

The cells of lymphoid origin all originated from samples taken from patients suffering from various pathological conditions classified according to the seat of the tumor proliferation. This proliferation takes place either in the bone marrow, for CLL, B-cell prolymphocytic leukemia and T-cell acute lymphoblastic leukemia (T-ALL); or in the lymph nodes for mantle cell lymphoma and marginal zone lymphoma. A classification can also be carried out according to the cell type affected: B lymphocytes (CLL, B-cell prolymphocytic leukemia, mantle cell lymphoma and marginal zone lymphoma) or T lymphocytes (T-ALL).

The cells of myeloid origin were taken from patients suffering from acute myeloid leukemia (2 patients).

The inventors first tested a leukemia line other than CLL: B-cell prolymphocytic leukemia (pro-ly, FIG. 7). As indicated in FIG. 7, these cells are sensitive to the A1WT peptide since the cell survival is only 20% after 24 H of treatment, close to the survival rate observed for the CLL cells. The A1WT peptide can therefore affect cells derived from various leukemia lines, including CLL and B-cell prolymphocytic leukemia.

Cancer cells which are of B type but which are not leukemia cells and which originate from malignant lymphomas of which the predominant origin is the lymph nodes were then tested. This involved mantle cell lymphoma (MAN, FIG. 7, 1 patient) and marginal zone lymphoma (MZL, 1 patient). The survival rate in the presence of the A1WT peptide is approximately 30% (FIG. 7), close to that observed for the CLL cells. The activity of the A1WT peptide is not therefore specific for cells derived from leukemic pathological conditions.

The effect of the A1WT peptide was then tested on T lymphocytes obtained by taking a sample from a patient suffering from T-cell acute lympoblastic leukemia (T-ALL, FIG. 7). The results show that the effect of the peptide is as great as for the CLL cells. The peptide therefore acts on both T-type and B-type cancer cells.

A myeloid line was then used. The A1WT peptide is active on cells taken from two patients suffering from acute myeloid leukemia (AML, FIG. 7) since a survival rate of 38% is observed. These results show that the peptide is not specific for lymphoid pathological conditions, but is also active on the myeloid lines tested.

The effect of the peptide was also tested on B and T lymphocytes (L.T and L.B, FIG. 7) obtained from peripheral blood taken from 6 patients suffering from a disease not related to a lymphocytic pathological condition, hemochromatosis. The results showed that the peptide also acts on these B and T lymphocytes, although the effect was greater on the B lymphocytes than on the T lymphocytes, with a survival rate, respectively, of 12% and 38% after 4 H of incubation with 40 µM of A1WT peptide (FIG. 7).

It is interesting to note that the peptide acts on cells blocked in G0-G1 (B lymphocytes originating from a patient suffering from CLL) and also on proliferating cells (all the lines used, except B lymphocytes, originating from a patient suffering from CLL).

Since the peptide is effective on many hematopoietic cancerous pathological conditions, the inventors then tested cells derived from a solid cancer, the HGT1 cell line derived from a gastric cancer. The effect of the peptide was weak, since more than 88% of the cells survive after 4 H treatment with the A1WT peptide (HGT1, FIG. 7). Likewise, the survival of cells derived from a human colon cancer or from a simian kidney cancer is barely affected by the peptide (respectively 94 and 90% cell survival). However, the results obtained on the cells derived from a human colon cancer or from a kidney cancer may be due to the technique used, namely flow cytometry, which is very suitable for cells in suspension but less so for adherent cells (such as cells of the COS7, HCT116 and HGT1 lines) which must be detached for analysis, the dead cells possibly being lost during the washes and not counted.

The inventors therefore completed these experiments using an identical cell labeling technique (namely the propidium iodide permeability test), but using a fluorescence microscopy approach, which makes it possible to quantify the cell mortality directly and to perform reliable kinetics. Thus, cells derived from the transformation, with adenovirus 5, of human embryo kidney cells (293) and derived from a cervical cancer (HeLa) were tested. The results show a dose-dependent effect of the peptide on the two lines tested, with a high sensitivity of the HeLa cells, comparable to that observed for the B lymphocytes derived from patients suffering from chronic lymphoid leukemia (JOK) (FIG. 10). The efficacy of the peptide is not therefore limited to hematopoietic cells.

Furthermore, the inventors observed that the effect of the peptide is extremely rapid, since as early as 15 min after addition of the peptide, the survival rate of the B lymphocytes derived from patients suffering from chronic lymphoid leukemia (JOK) goes from 98 to 70% (FIG. 11).

In order to classify the cells according to their sensitivity to the peptide, the cells were exposed to various concentrations of A1 WT IRS peptide (FIG. 8). For all the cells analyzed, the cell survival rate decreases when the peptide concentration increases.

In terms of degree of response of the peptide, 3 groups of cell populations can be defined, according to the cell survival rate compared with cells incubated without peptide, after 4 H of incubation with 20 µM of peptide:

cells which respond weakly, cell survival greater than 90%: acute myeloid leukemia (AML) and cells derived from gastric, colon or renal cancers.

cells which show a partial response, cell survival between 75 and 90%: marginal zone lymphoma (MZL), mantle cell lymphoma, control T lymphocytes.

cells which show a strong response, cell survival less than 65%: CLL, B-cell prolymphocytic leukemia, control B lymphocytes, T-cell acute lymphoblastic leukemia (T-ALL).

In conclusion, the A1WT peptide could open up therapy perspectives for various cancerous pathological conditions, in particular hematopoietic cancerous pathological conditions.

Example 6: Analysis of the Effect of Various Mutants Obtained from the A1 Peptide on CLL Lymphocytes Taken from Patients The inventors then prepared a series of variant peptides obtained by (conservative or nonconservative) substitution of one or two amino acids of the A1 peptide, or by deletion of the first two amino acids. The list of peptides tested in this new series of experiments is indicated hereinafter:

TABLE 1

Presentation of the sequence of the peptides and of their cell effect

| Peptide | Sequence | SEQ ID No | CLL 40 | LT 40 | Jok 20 | Jok 40 |
|---|---|---|---|---|---|---|
| A1 WT IRS | RRKYGRDFLLRFRYIRS | 2 | + | + | + | + |
| A1 YALA IRS | RRKAGRDFAARFRYIRS | 6 | − | − | − | − |
| A1 K3I IRS | RRIYGRDFLLRFRYIRS | 11 | − | nd | +/− | + |
| A1 del2 IRS | KYGRDFLLRFRYIRS | 12 | − | − | +/− | + |
| A1 R1, 2K IRS | KKKYGRDFLLRFRYIRS | 13 | + | +/− | +/− | + |
| A1 R1, 2G IRS | GGKYGRDFLLRFRYIRS | 14 | − | − | − | +/− |
| A1 K3R IRS | RRRYGRDFLLRFRYIRS | 15 | + | + | + | + |
| A1 G5A-IRS | RRKYARDFLLRFRYIRS | 16 | + | + | + | + |
| A1 G5S IRS | RRKYSRDFLLRFRYIRS | 17 | + | + | + | + |
| A1 R6K IRS | RRKYGKDFLLRFRYIRS | 18 | + | +/− | +/− | + |
| A1 R6H IRS | RRKYGHDFLLRFRYIRS | 19 | +/− | +/− | + | + |
| A1 D7E IRS | RRKYGREFLLRFRYIRS | 20 | + | + | + | + |
| A1 D7A IRS | RRKYGRAFLLRFRYIRS | 21 | + | + | + | + |
| A1 F12K IRS | RRKYGRDFLLRKRYIRS | 22 | − | − | − | − |
| A1 F12W IRS | RRKYGRDFLLRWRYIRS | 23 | + | + | + | +/− |
| BP2 WT IRS | RIIYDRKFLLDRRYIRS | 7 | − | nd | − | − |
| BP2 I3K IRS | RIKYDRKFLLDRRYIRS | 24 | − | − | − | − |

1st column: peptide name
2nd column: peptide sequence, the amino acids that have been mutated relative to the sequence of A1 WT IRS are indicated in bold. The A1 YALA IRS peptide corresponds to the Y4AL9, 10A mutations in the A1 WT IRS sequence.
3rd column: sequence number.
Subsequent columns: level of effect of the peptides for inducing the mortality of B lymphocytes of CLL patients at 40 µM (CLL 40 column), of control T lymphocytes at 40 µM (LT40 column), of Jok cells at 20 µM (Jok 20 column) or at 40 µM (Jok column).
+: survival <25%,
+/−: survival between 25 and 50%,
−: survival >50%,
n.d: not determined; this percentage cell survival corresponds to the percentage of cells not labeled (either with annexin or with propidium iodide), evaluated by flow cytometry, after 4 hours of culture in the presence of peptide. The control sample corresponds to the cells incubated without peptide.

The peptides were tested on B lymphocytes from patients suffering from chronic lymphoid leukemia, control T lymphocytes, or Jok cells (cell line derived from B lymphocytes). The experiment was repeated three times for each type of cell tested.

The cells incubated without peptide exhibited a percentage survival of greater than 96% (control, FIG. 9).

The A1 WT IRS peptide (SEQ ID No: 2) induces, at 40 µM, a high cell mortality in the CLL cells and the Jok cells (FIG. 9 and table 1); the survival rate is higher in the control T cells as already described in the previous experiments (FIGS. 7 and 8).

The A1 YALA IRS peptide (SEQ ID No: 6, corresponding to Y4AL9AL10A A1 IRS), used as a negative control since it does not bind to eIF4E, as expected has no effect.

The A1 del2 IRS peptide (SEQ ID No: 12): the deletion of the first two amino acids of the sequence of A1 WT IRS causes loss of effect of the peptide at 40 µM on the CLL cells and the control T lymphocytes, and also on the Jok cells at 20 µM. At 40 µM, it nevertheless causes a considerable mortality on the Jok cells.

The A1 R1, 2K IRS peptide (SEQ ID No: 13): the replacement of the two arginines (RR) with two lysine amino acids (KK) decreases the effect at 40 µM in the CLL cells and the control T lymphocytes, and also on the Jok cells at 20 µM. At 40 µM, it has the same effect as the A1 WT IRS peptide on the Jok cells.

The A1 R1, 2G IRS peptide (SEQ ID No: 14): the substitution of the first two amino acids with two glycine neutral amino acids (GG) abolishes the effect of the peptide, except in the Jok cells when it is used at 40 µM where its effect is only partially decreased.

The A1 K3R IRS peptide (SEQ ID No: 15) and the A1 K3I IRS peptide (SEQ ID No: 11): the substitution of the lysine amino acid at position 3 with an arginine (R) does not modify the effect of the peptide in the three cell types, whereas the substitution of the same amino acid with an isoleucine (I) causes loss of effect of the peptide at 40 µM on the CLL cells, and also partially on the Jok cells at 20 µM.

The A1 G5A IRS peptide (SEQ ID No: 16) and the A1 G5S IRS peptide (SEQ ID No: 17): the substitution of the glycine amino acid (G) at position 5 with an alanine amino acid (A) or with a serine (S) slightly increases the effect of the peptide in the three cell types.

The A1 R6K IRS peptide (SEQ ID No: 18) and the A1 R6H IRS peptide (SEQ ID No: 19): the substitution of the R (arginine) amino acid at position 6 with the lysine (K) amino acid partially decreases the action of peptides in the three cell types, whereas its substitution with histidine (H) abolishes the effect on the CLL cells and the control T lymphocytes, contrary to the Jok cells, where the effect is potentiated.

The A1 D7E IRS peptide (SEQ ID No: 20) and the A1 D7A IRS peptide (SEQ ID No: 21): the substitution of the aspartic acid amino acid at position 7 with glutamic acid (E) or alanine (A) amino acids does not modify the effect of peptides in the CLL cells and the healthy T lymphocytes, except for the D7E peptide in the Jok cells, where its effect is potentiated.

The A1 F12K IRS peptide (SEQ ID No: 22) and the A1 F12W IRS peptide (SEQ ID No: 23): the substitution of the phenylalanine (F) amino acid at position 12 with the lysine (K) amino acid completely abolishes the action of the peptide in the three cell types, whereas its replacement with a tryptophan (W) does not modify the action of peptides in the three cell types.

The BP2 WT IRS peptide (SEQ ID No: 7) corresponds to the eIF4E binding sequence of the human 4E-BP2 protein. 4E-BP2 is a protein known to interact with eIF4E (chosen for its affinity for eIF4E which is greater than 4E-BP1 (Ptushkina, EMBO J, 1999)). This peptide has no effect either on the CLL cells or on the Jok cells.

The BP2 I3K IRS peptide (SEQ ID No: 24): it is the BP2 sequence mutated at position 3. An isoleucine is present at position 3 of BP2 and SBP, whereas a lysine is present at this position in the sequence of A1 WT. The inventors tested whether this difference could be responsible for the difference in cell effect between A1 WT and BP2 WT. The results show that the substitution of the isoleucine (I) amino acid at position 3 of BP2WT with the lysine (K) amino acid does not confer a better efficacy on the latter.

Although the BP2 peptide effectively inhibits eIF4E-dependent translation (FIG. 2), it has no effect on cell survival. The ability of a peptide to bind to eIF4E and to inhibit translation is not therefore sufficient to lead to the cell mortality observed with A1WT.

Moreover, the inventors synthesized a peptide A1 G5AD7A IRS (SEQ ID No: 30) having simultaneously the G5A and D7A substitutions mentioned above. The action of the peptide is similar to that obtained for A1 G5A IRS and A1 D7A IRS.

In conclusion, the mutations of the peptide can decrease or increase the efficacy of the peptide in inducing cell death, in a manner dependent on the cell type analyzed. In particular:

a) The first two amino acids are necessary for the activity of the peptide, and should preferably be basic amino acids, for example arginines.

b) The amino acid at position 3 should also be chosen from basic amino acids (R, K, H).

c) A serine or an alanine should preferably be chosen at position 5.

d) An arginine (R) will preferably be chosen at position 6. A histidine will be preferred for a lesser CLL and control-T-lymphocyte effect compared with Jok cells.

e) The mutation tested at position 7 has no effect. If a lesser effect on the Jok cells is desired compared with the effect on the CLL cells and control T lymphocytes, glutamic acid (E) is to be avoided.

f) The amino acid at position 12 will be phenylalanine (F) or tryptophan (W).

REFERENCES

References

Boumsell, L., Bernard, A., Lepage, V., Degos, L., Lemerle, J. and Dausset, J. (1978) Some chronic lymphocytic leukemia cells bearing surface immunoglobulins share determinants with T cells. *Eur J Immunol*, 8, 900-904.

Caligaris-Cappio, F. and Hamblin, T. J. (1999) B-cell chronic lymphocytic leukemia: a bird of a different feather. *J Clin Oncol*, 17, 399-408.

Cormier, P., Pyronnet, S., Salaun, P., Mulner-Lorillon, O. and Sonenberg, N. (2003) Cap-dependent translation and control of the cell cycle. *Prog Cell Cycle Res*, 5, 469-475.

Cowell, S. M., Lee, Y. S., Cain, J. P. and Hruby, V. J. (2004) Exploring Ramachandran and chi space: conformationally constrained amino acids and peptides in the design of bioactive polypeptide ligands. *Curr Med Chem*, 11, 2785-2798.

Culjkovic, B., Topisirovic, I., Skrabanek, L., Ruiz-Gutierrez, M. and Borden, K. L. (2005) eIF4E promotes nuclear export of cyclin D1 mRNAs via an element in the 3'UTR. *J Cell Biol*, 169, 245-256.

Delmer, A., Ajchenbaum-Cymbalista, F., Tang, R., Ramond, S., Faussat, A. M., Marie, J. P. and Zittoun, R. (1995) Overexpression of cyclin D2 in chronic B-cell malignancies. *Blood*, 85, 2870-2876.

Deshayes, S., Morris, M., Heitz, F. and Divita, G. (2008) Delivery of proteins and nucleic acids using a non-covalent peptide-based strategy. *Adv Drug Deliv Rev*, 60, 537-547.

Dong, C., Li, Q., Lyu, S. C., Krensky, A. M. and Clayberger, C. (2005) A novel apoptosis pathway activated by the carboxyl terminus of p21. *Blood*, 105, 1187-1194.

Fialkow, P. J., Najfeld, V., Reddy, A. L., Singer, J. and Steinmann, L. (1978) Chronic lymphocytic leukaemia: Clonal origin in a committed B-lymphocyte progenitor. *Lancet*, 2, 444-446.

Foged, C. and Nielsen, H. M. (2008) Cell-penetrating peptides for drug delivery across membrane barriers. *Expert Opin Drug Deliv*, 5, 105-117.

Fu, S. M., Winchester, R. J. and Kunkel, H. G. (1975) Similar idiotypic specificity for the membrane IgD and IgM of human B lymphocytes. *J Immunol*, 114, 250-252.

Hanasaki, K., Powell, L. D. and Varki, A. (1995) Binding of human plasma sialoglycoproteins by the B cell-specific lectin CD22. Selective recognition of immunoglobulin M and haptoglobin. *J Biol Chem*, 270, 7543-7550.

Herbert, T. P., Fahraeus, R., Prescott, A., Lane, D. P. and Proud, C. G. (2000) Rapid induction of apoptosis mediated by peptides that bind initiation factor eIF4E. *Curr Biol*, 10, 793-796.

Holcik, M. and Sonenberg, N. (2005) Translational control in stress and apoptosis. *Nat Rev Mol Cell Biol*, 6, 318-327.

Kanovsky, M., Raffo, A., Drew, L., Rosal, R., Do, T., Friedman, F. K., Rubinstein, P., Visser, J., Robinson, R., Brandt-Rauf, P. W., Michl, J., Fine, R. L. and Pincus, M. R. (2001) Peptides from the amino terminal mdm-2-binding domain of p53, designed from conformational analysis, are selectively cytotoxic to transformed cells. *Proc Natl Acad Sci USA*, 98, 12438-12443.

Koromilas, A. E., Lazaris-Karatzas, A. and Sonenberg, N. (1992) mRNAs containing extensive secondary structure in their 5' non-coding region translate efficiently in cells overexpressing initiation factor eIF-4E. *Embo J*, 11, 4153-4158.

Malik, D. K., Baboota, S., Ahuja, A., Hasan, S. and Ali, J. (2007) Recent advances in protein and peptide drug delivery systems. *Curr Drug Deliv*, 4, 141-151.

Moerke, N. J., Aktas, H., Chen, H., Cantel, S., Reibarkh, M. Y., Fahmy, A., Gross, J. D., Degterev, A., Yuan, J., Chorev, M., Halperin, J. A. and Wagner, G. (2007) Small-molecule inhibition of the interaction between the translation initiation factors eIF4B and eIF4G. *Cell*, 128, 257-267.

Moreau, E. J., Matutes, E., A'Hern, R. P., Morilla, A. M., Morilla, R. M., Owusu-Ankomah, K. A., Seon, B. K. and Catovsky, D. (1997) Improvement of the chronic lymphocytic leukemia scoring system with the monoclonal antibody SN8 (CD79b). *Am J Clin Pathol*, 108, 378-382.

Morley, S. J., Caldwell, M. J. and Clemens, M. J. (2005) Initiation factor modifications in the preapoptotic phase. *Cell Death Differ*, 12, 571-584.

O'Brien, S., del Giglio, A. and Keating, M. (1995) Advances in the biology and treatment of B-cell chronic lymphocytic leukemia. *Blood*, 85, 307-318.

Preud'homme, and Seligmann, M. (1972) Immunoglobulins on the surface of lymphoid cells in Waldenstrom's macroglobulinemia. *J Clin Invest*, 51, 701-705.

Richter, J. D. and Sonenberg, N. (2005) Regulation of cap-dependent translation by eIF4E inhibitory proteins. *Nature*, 433, 477-480.

Soares, A. F., Carvalho Rde, A. and Veiga, F. (2007) Oral administration of peptides and proteins: nanoparticles and cyclodextrins as biocompatible delivery systems. *Nanomed*, 2, 183-202.

Topisirovic, I., Kentsis, A., Perez, J. M., Guzman, M. L., Jordan, C. T. and Borden, K. L. (2005) Eukaryotic translation initiation factor 4E activity is modulated by HOXA9 at multiple levels. *Mol Cell Biol*, 25, 1100-1112.

Vrhovac, R., Delmer, A., Tang, R., Marie, J. P., Zittoun, R, and Ajchenbaum-Cymbalista, F. (1998) Prognostic significance of the cell cycle inhibitor p27Kip1 in chronic B-cell lymphocytic leukemia. *Blood*, 91, 4694-4700.

The invention claimed is:

1. A method of treating a malignant hematopoietic disease selected from the group consisting of chronic lymphoid leukemia, B-cell prolymphocytic leukemia, T-cell acute lymphoblastic leukemia, marginal zone lymphoma and mantle cell lymphoma, comprising administering to a patient in need thereof an isolated peptide comprising the sequence $X_1X_2X_3YX_4X_5X_6X_7LX_8X_9X_{10}$ (SEQ ID NO: 1), in which:

$X_1$ and $X_2$ represent, independently of one another, an amino acid chosen from R, K and H, $X_3$ represents an amino acid chosen from R, K and H, $X_4$, $X_5$ and $X_6$ represent any amino acid, $X_7$ represents an amino acid chosen from F, A, V, L, I and M, $X_8$ represents an amino acid chosen from L, M and F, $X_9$ represents any amino acid, and $X_{10}$ represents an amino acid chosen from F, Y, W and H.

2. The method as claimed claim 1, wherein:

$X_1=X_2=R$, and/or $X_3=K$ or R, and/or $X_4=G$, A or S, and/or $X_5=R$ or H, and/or $X_6=D$, E, A, V, L, P, M, F or I, and/or $X_7=F$, and/or $X_8=L$, and/or $X_9=R$, and/or $X_{10}=F$ or W.

3. The method as claimed claim 1, wherein:
$X_4$=A or S, and/or
$X_5$=R, and/or
$X_6$=D or A.

4. The method as claimed in claim 1, wherein:
$X_1$=$X_2$=R,
$X_3$=K or R,
$X_4$=G, A or S,
$X_5$=R or H,
$X_6$=D, E, A, V, L, P, M, F or I,
$X_7$=F,
$X_8$=L,
$X_9$=R, and
$X_{10}$=F or W.

5. The method as claimed in claim 1, wherein:
$X_4$=A or S,
$X_5$=R, and
$X_6$=D or A.

6. The method as claimed in claim 1, wherein a peptide sequence that promotes entry of said second peptide into eukaryotic cells is bonded to the C-terminal end of the sequence SEQ ID NO:1.

7. The method as claimed in claim 6, wherein the peptide sequence that promotes entry of said second peptide into eukaryotic cells is SEQ ID NO:4.

8. The method as claimed in claim 1, wherein the isolated peptide which is administered to the patient is SEQ ID NO:2.

9. The method as claimed in claim 1, wherein the isolated peptide which is administered to the patient also comprises one or more protective group(s) at the N- and/or C-terminal end.

10. The method as claimed in claim 1, wherein the isolated peptide which is administered to the patient is cyclized.

11. An isolated peptide comprising the sequence $X_1X_2X_3YX_4X_5X_6X_7LX_8X_9X_{10}$ (SEQ ID NO: 1) and a second peptide sequence that promotes entry of said peptide into eukaryotic cells, directly bonded to the C-terminal end of the sequence SEQ ID NO: 1, wherein:
$X_1$ and $X_2$ represent, independently of one another, an amino acid chosen from R, K and H,
$X_3$ represents an amino acid chosen from R, K and H,
$X_4$, $X_5$ and $X_6$ represent any amino acid,
$X_7$ represents an amino acid chosen from F, A, V, L, I and M,
$X_8$ represents an amino acid chosen from L, M and F,
$X_9$ represents any amino acid, and
$X_{10}$ represents an amino acid chosen from F, Y, W and H.

12. The isolated peptide as claimed in claim 11, wherein the second peptide sequence that promotes entry of said peptide into eukaryotic cells is SEQ ID NO:4.

13. The isolated peptide as claimed in claim 12, wherein the peptide comprises the sequence of SEQ ID NO:2.

14. The isolated peptide as claimed in claim 11, wherein the peptide also comprises one or more protective group(s) at the N- and/or C-terminal ends.

15. A pharmaceutical composition comprising the isolated peptide as claimed in claim 11.

16. The isolated peptide as claimed in claim 11, wherein:
$X_1$=$X_2$=R, and/or
$X_3$=K or R, and/or
$X_4$=G, A or S, and/or
$X_5$=R or H, and/or
$X_6$=D, E, A, V, L, P, M, F or I, and/or
$X_7$=F, and/or
$X_8$=L, and/or
$X_9$=R, and/or
$X_{10}$=F or W.

17. The isolated peptide as claimed in claim 11, wherein:
$X_4$=A or S, and/or
$X_5$=R, and/or
$X_6$=D or A.

18. The isolated peptide as claimed in claim 16, wherein:
$X_1$=$X_2$=R, and
$X_3$=K or R, and
$X_4$=G, A or S, and
$X_5$=R or H, and
$X_6$=D, E, A, V, L, P, M, F or I, and
$X_7$=F, and
$X_8$=L, and
$X_9$=R, and
$X_{10}$=F or W.

19. The isolated peptide as claimed in claim 17, wherein:
$X_4$=A or S, and
$X_5$=R, and
$X_6$=D or A.

* * * * *